United States Patent
Echner

(10) Patent No.: US 8,718,234 B2
(45) Date of Patent: May 6, 2014

(54) MULTI-LEAF COLLIMATOR WITH LEAF DRIVE

(71) Applicant: Deutsches Krebsforschungszentrum, Heidelberg (DE)

(72) Inventor: Gernot Echner, Wiesenbach (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 13/930,572

(22) Filed: Jun. 28, 2013

(65) Prior Publication Data

US 2013/0284951 A1    Oct. 31, 2013

Related U.S. Application Data

(63) Continuation of application No. PCT/EP2011/073051, filed on Dec. 16, 2011.

(30) Foreign Application Priority Data

Dec. 29, 2010   (EP) ..................................... 10197257

(51) Int. Cl.
*G21K 1/04*   (2006.01)
(52) U.S. Cl.
CPC ...................................... *G21K 1/04* (2013.01)
USPC .......................... 378/152; 378/153; 250/505.1
(58) Field of Classification Search
USPC ...................... 250/505.1; 378/152, 153, 150
See application file for complete search history.

(56) References Cited

U.S. PATENT DOCUMENTS 5,835,555 A * 11/1998 Barry et al. .................... 378/146
7,783,007 B2 * 8/2010 Echner ............................ 378/65

OTHER PUBLICATIONS

International Patent Application PCT/EP2011/073051 International Preliminary Report on Patentability/Written Opinion mailed Jul. 11, 2013.

* cited by examiner

*Primary Examiner* — Kiet T Nguyen
(74) *Attorney, Agent, or Firm* — Woodard, Emhardt, Moriarty, McNett & Henry LLP

(57) ABSTRACT

A multi-leaf collimator includes leaf drives and two sets of displaceable leaves arranged side by side and facing each other to impress a high-energy beam with the shape of an irregularly formed treatment object. Each of the leaves assumes a position oriented along the shape of the treatment object by means of a leaf drive and each are equipped with a gear rod-like drive engagement in the direction of the displacement. A leaf-side pivotable gear segment is located, together with a motor-side gear segment, on a segment disk that engages with the gear rod-like drive engagement. A pinion drivable by a motor engages with the motor-side gear segment. The segment discs are arranged side by side for each set of leaves as a package on one axis. The motor-side gear segments of two segment disks located next to each other are staggered so that they will not abut each other.

42 Claims, 15 Drawing Sheets

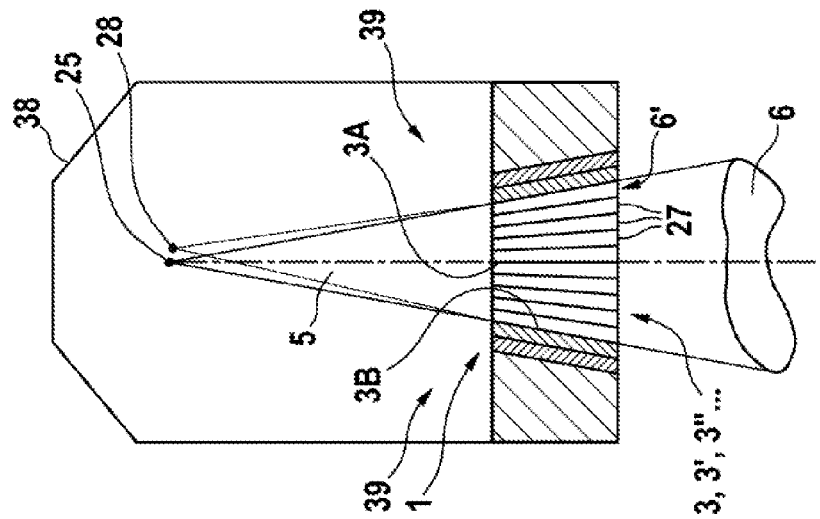
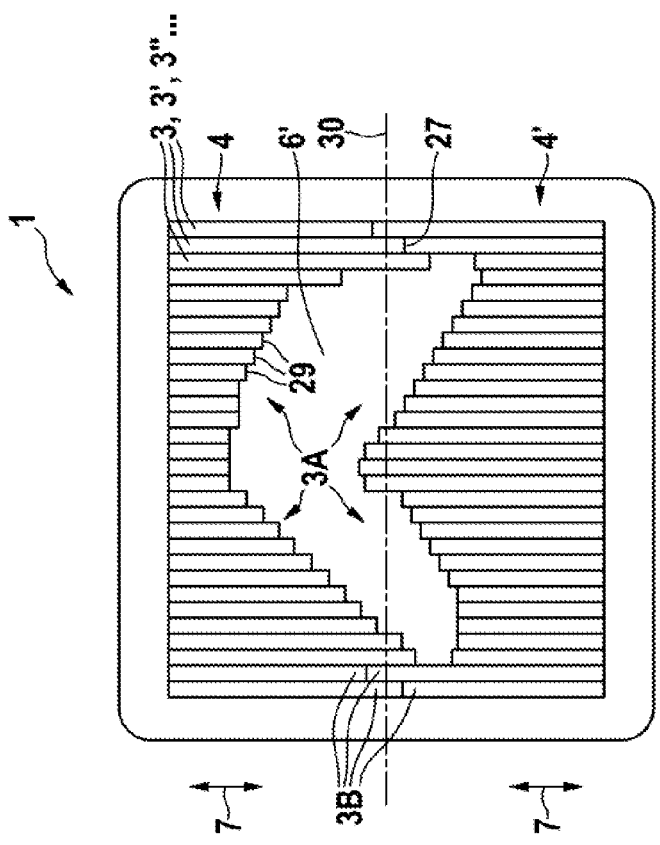

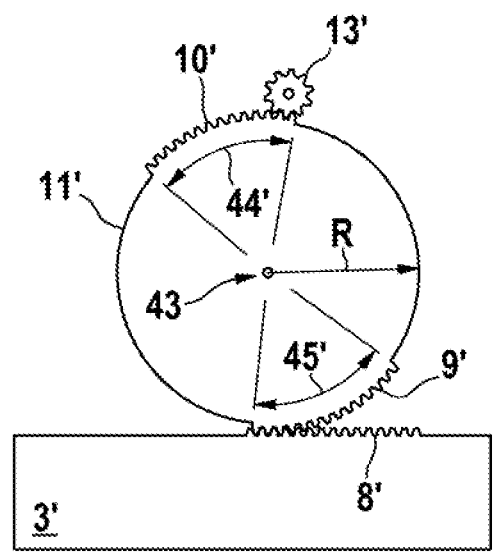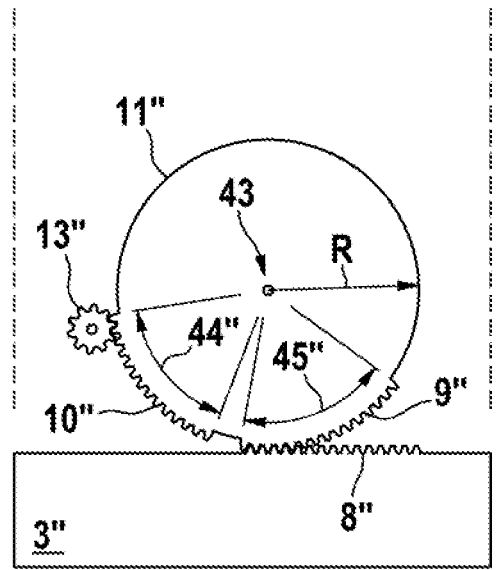
Fig. 11A

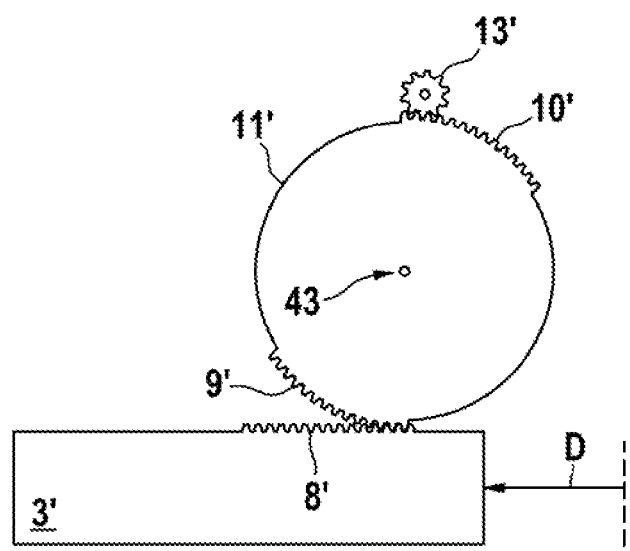
Fig. 11B
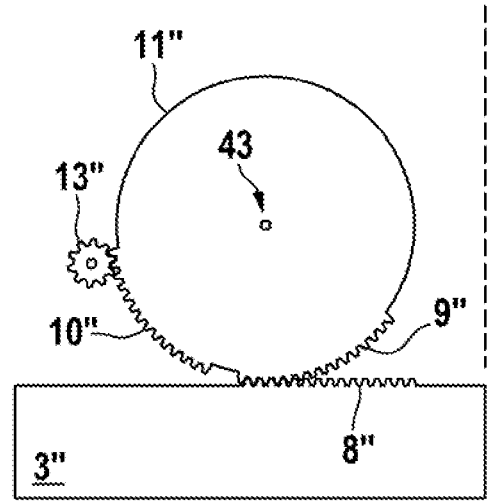

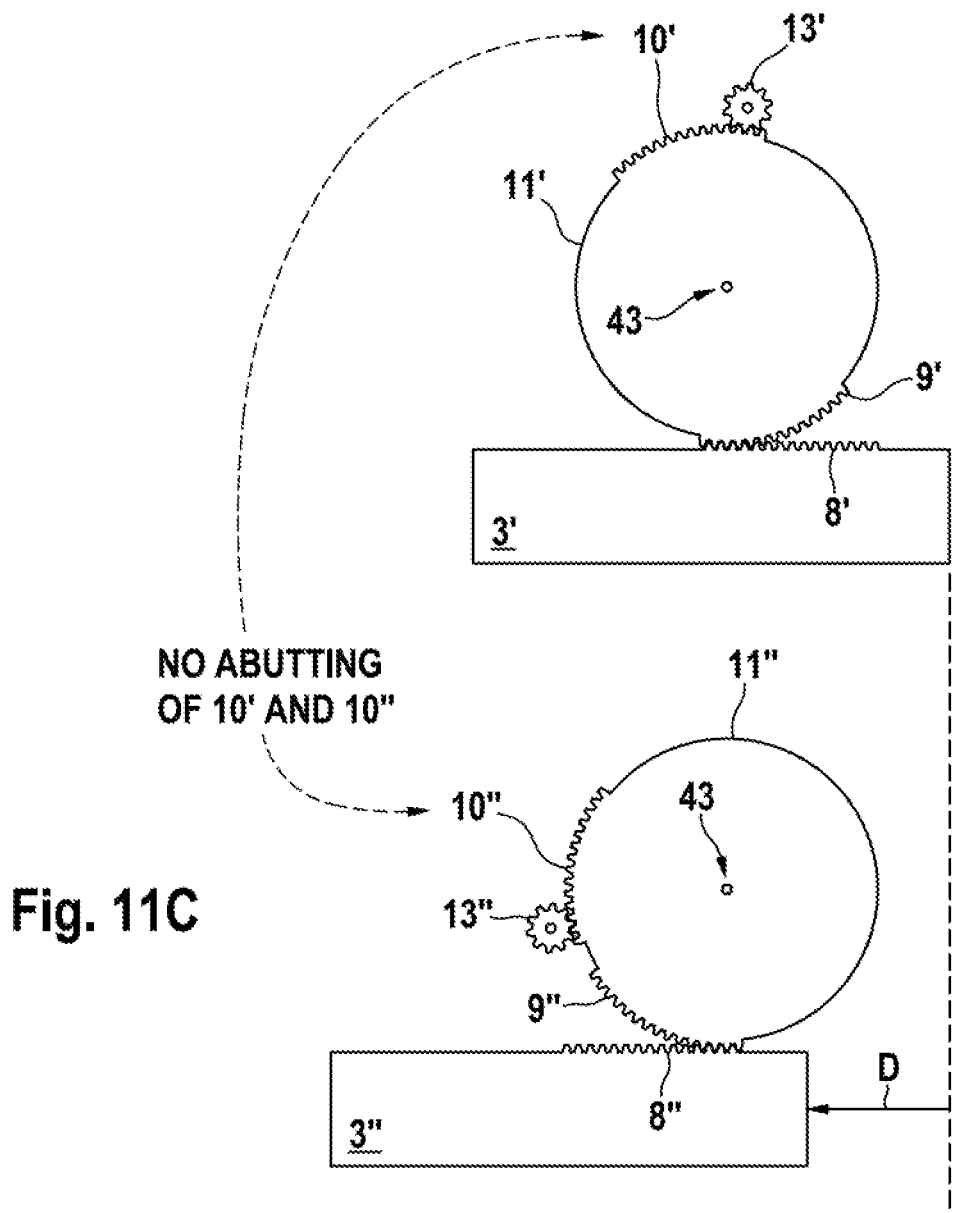

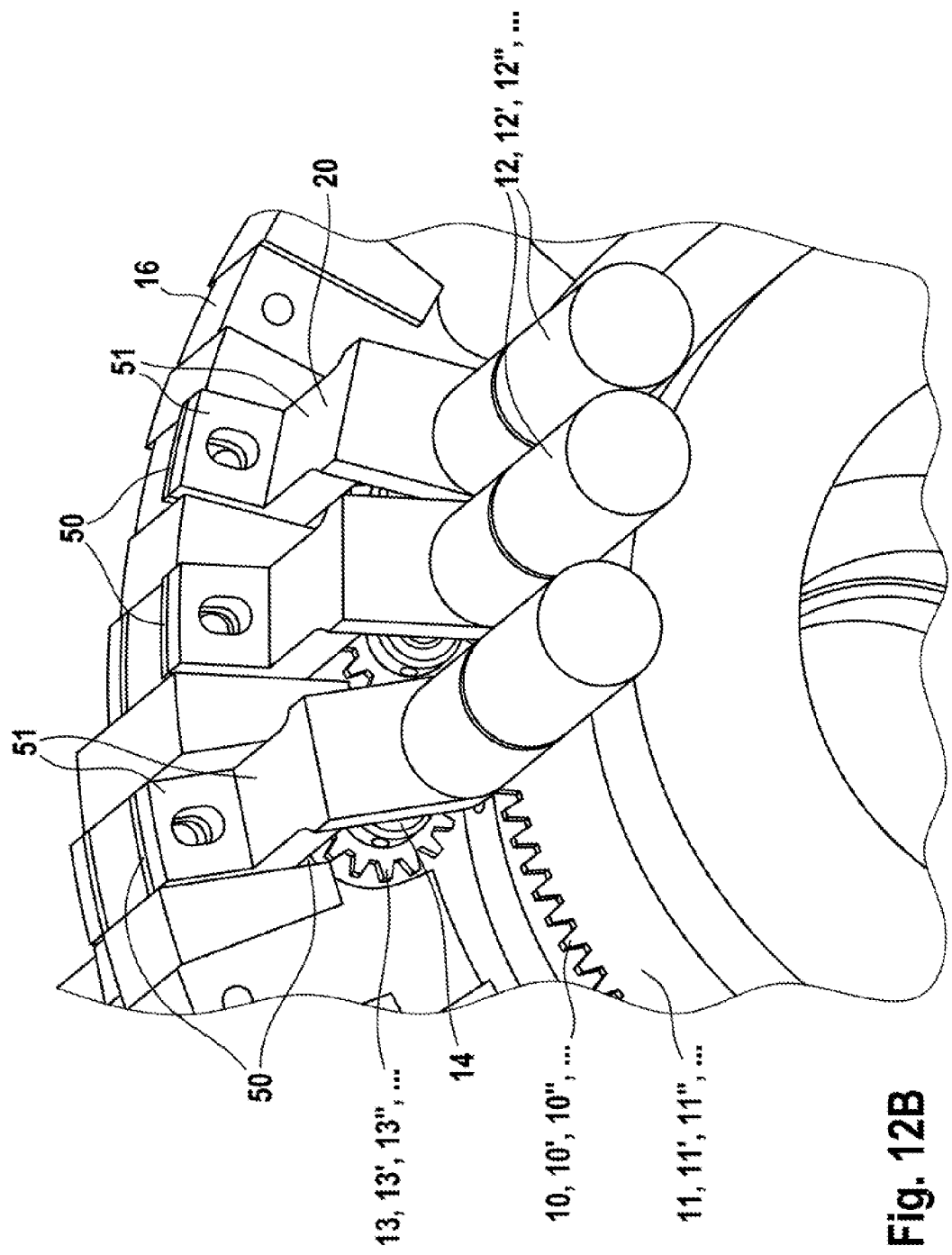

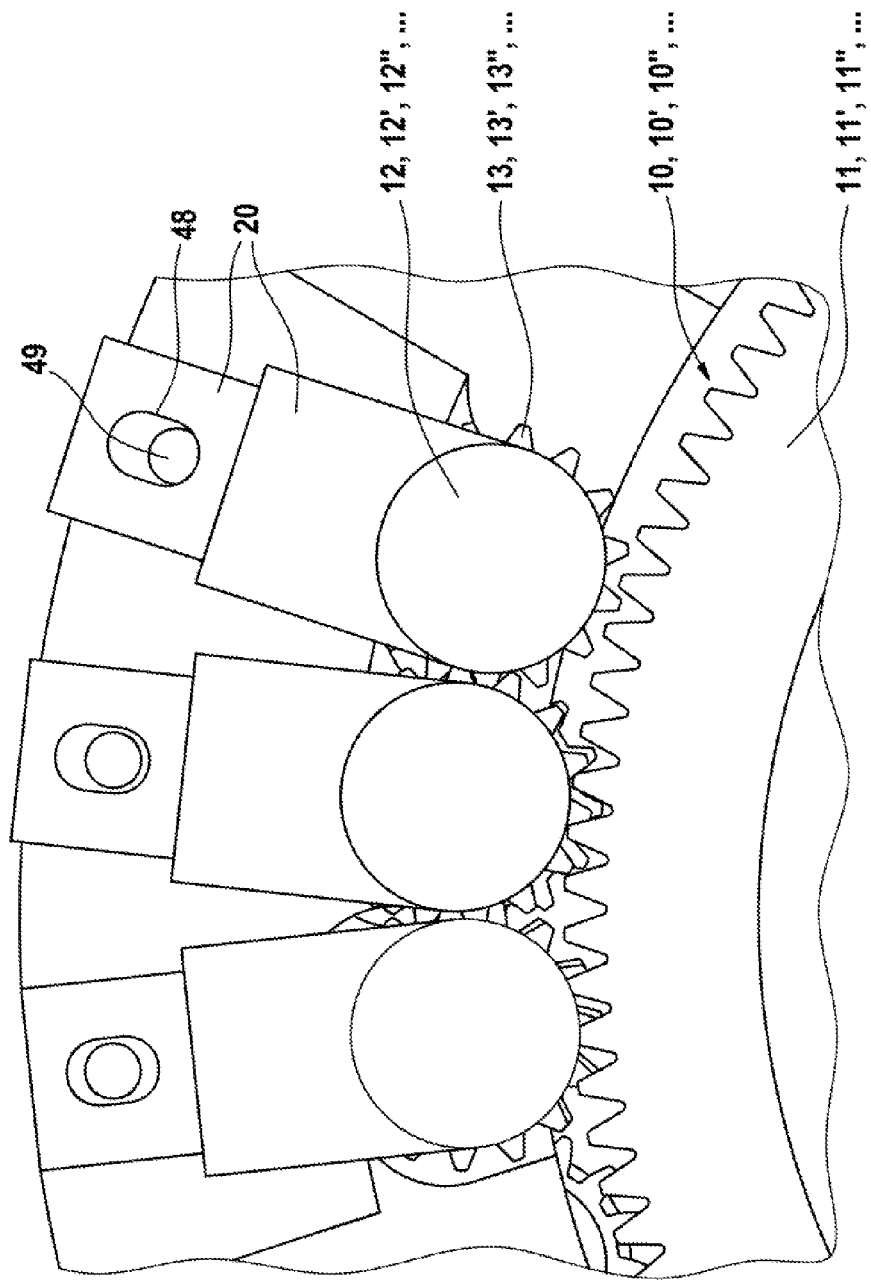

MULTI-LEAF COLLIMATOR WITH LEAF DRIVE

CROSS-REFERENCE TO RELATED APPLICATION

This application is a continuation of International Application No. PCT/EP2011/073051, filed Dec. 16, 2011, which claims the benefit of European Patent Application No. 10 197 257.8 filed Dec. 29, 2010, which are hereby incorporated by reference.

BACKGROUND

The invention relates to a multi-leaf collimator, preferably for controlling a shape of a high-energy radiation beam emanating from a radiation source and propagating in a direction of propagation. In a preferred aspect, the invention relates to a multi-leaf collimator with leaf drives, with two sets of displaceable leaves arranged side by side facing each other in order to impress a high-energy beam with the shape of an irregularly formed treatment object by enabling each of the leaves to assume a position oriented along the shape of the treatment object by means of a leaf drive, with the leaf drives being designed in such a way that the each of the leaves is each equipped with a gear rod-like drive engagement in the direction of the displacement. As known in the art, the term "gear-rod-like drive engagement" can also be referenced by the English term "rack" or "rack gear".

The treatment devices used today in oncological radiation therapy are equipped with collimators that delimit high-energy beams, in most cases high energy radiation of a linear accelerator, in such a way that the beams have exactly the same shape as the treatment object. Since such radiation, e.g. of a tumor, occurs from various directions, it is possible to achieve a great irradiation intensity of the tumor and, at the same time, to stress the surrounding tissue only to a limited extent.

The leaves of the multi-leaf collimator may also be called "shutter blades" or "lamellae". The multi-leaf collimators may also be called contour collimators since due to the positioning of the leaves, contours of treatment objects, for example tumors, can be recreated for each beam application, each of which occurs from a certain solid angle. This is important in order to protect the adjacent healthy tissue to the greatest extent possible. In the case of critical tissue such as nerves, this is particularly necessary in order to preserve their functional capability.

A multi-leaf collimator of the kind mentioned at the beginning has been known, for example, from EP 0 387 921 A2. Since in the case of such multi-leaf collimators, each leaf must be moved into a certain position, in most cases a drive must be assigned to each leaf. In the case of the aforementioned publication, not every leaf is assigned a motor, which is why the leaves are arranged in series by means of drive couplings and locking devices. However, it has also been known to assign an electric motor to each leaf that positions the leaves via a pinion and a gear rod-like drive engagement.

However, the more precisely the shape of the treatment object, e.g. of a tumor, is to be recreated, the more and thinner leaves will be required. This means that a large number of electric motors and drive transmissions to the leaves must be housed in an extremely small space. In addition, these drives must be arranged in one area in such a way that they will be located within an irradiation head containing the radiations source and the collimator in an area in which structural space is available.

Since for an irradiation, the irradiation head usually must be moved into various solid angles relative to the target volume, e.g. the tumor, it is desirable to design such a collimator as compact and lightweight as possible. In this way, a gantry or a robot arm that move the irradiation head into these solid angle positions can also be constructed with less weight, thereby making them faster movable into various positions and more mobile.

SUMMARY

The invention is therefore based on the objective of designing a multi-leaf collimator of the kind mentioned at the beginning in such a way that the leaf drives will be constructed as compact and lightweight as possible and attached to the collimator in such a way that they will be located in an available structural space of an irradiation head.

This is achieved in accordance with the invention by the subject-matter disclosed in the independent claims. Preferred embodiments which may be realized and isolated way or in combination with other preferred embodiments are disclosed herein.

In a first aspect of the present invention, a multi-leaf collimator is disclosed, with leaf drives, with two sets of displaceable leaves arranged side by side of each other and facing each other in order to impress a high-energy beam with the shape of an irregularly formed treatment object by enabling each of the leaves to assume a position oriented along the shape of the treatment object by means of the leaf drives. The leaf drives are designed in such a way that the leaves are each equipped with a gear rod-like drive engagement in a direction of the displacement, wherein a pivotable leaf-side gear segment located, together with a motor-side gear segment on a segment disk, engages with the gear rod-like drive engagement, with a pinion drivable by a motor engaging with the motor-side gear segment; wherein the segment disks are arranged side by side for each set of leaves as a package on one axis; and wherein the motor-side gear segments of two segment disks located next to each other are staggered in such a way that they will not abut each other.

Preferably, the pinions are wider than the motor-side gear segments.

Preferably, two or more segment disks may form segment disk packages. Preferably, the motors for each package of segment discs may be arranged in series in the shape of an arch. Preferably, the motors for each package of segment discs in an engagement range of the respective motor-side gear segments are arranged in series in the shape of an arch. Preferably, the motors are mounted on a bearing block which encompasses in each case a package of segment discs in their circumferential range. Further preferably, a step-like gradation of an arrangement of the pinions driven by the motors is provided for their engagement with the various motor-side gear segments. Further preferably, at least two step-like gradations are provided, with segment discs located next to each other being driven by motors with pinions assigned to various ones of these step-like gradations and the motor-side gear segments of segment discs lying next to each other being located in different areas of the circumference of the package of segment discs.

Relative to its width, the gear rod-like drive engagement of the leaves preferably may be designed differently from the width of the leaf-side gear segment.

The bearing block may be equipped on both sides with motors.

The radii of all segment disks may be identical. Alternatively, two or more of the segment disks may have differing radii. Similarly, the radii of all of the pinions may be identical. Alternatively, two or more pinions may have differing radii. By using differing radii of the segment disks and/or of the pinions, a stacked arrangement of the motors may be achieved.

Preferably, due to the preferred arrangement of motor-side gear segments on corresponding varying radii of the segment discs, the motors are arranged in arch-shaped sequences lying on top of each other.

The bearing block may position the pinions indirectly or directly by means of positioning agents in their engagement position opposite the motor-side gear segments. Preferably, the pinions are mounted on axles supported by motor bearings and the latter are mounted on the bearing block.

Preferably, the motor bearings each comprise a motor holder for mounting the motor and an axle bearing for bearing the axle. The motor holder and the axle bearing may be made of the same or different materials. Consequently, by choosing appropriate materials for both elements, the properties of these elements may be adjusted separately, such as with regard to their weight and/or with regard to their stability against abrasion and/or with regard to their friction properties. As an example, the motor holders may fully or partially be made of a material lighter than the material of the axle bearings. Preferably, the motor holders may fully or partially be made of one or more of the group consisting of aluminum and titanium, in order to reduce the weight of the multi-leaf collimator. The axle bearings may fully or partially be made of a heavier material, such as one or more of the materials chosen from the group consisting of bronze and brass, specifically bearing bronze. By using a material for motor holder lighter than a material used for the axle bearing, some significant weight reduction may be achieved, in view of the typically large number of motors and axles, such as 80 motors or even more. Further, by using separate parts for the axle bearings and the motor holders, manufacturing of the motor bearings may be simplified and production costs may be reduced. Additionally or alternatively, the axle bearings may fully or partially be made of a material adapted to provide low friction, preferably even without the use of an additional lubricant. Thus, the axle bearings may fully or partially be made of a plastic material.

In a further preferred embodiment, the leaf drives may be mounted adjustably, i.e. may be mounted such that a position of the leaf drives relative to the leaves may be adjusted. Preferably, a distance between the leaf drives and the leaves may be adjustable by an appropriate adjustable mounting of the leaf drives. Many ways of adjustable mounting are known to the skilled person. In a preferred embodiment, the adjustable mount comprises at least one excenter mount, such that the position of one or more or all of the leaf drives is adjustable by at least one excenter. Again, by providing the adjustability, manufacturing may be simplified since manufacturing tolerances may be compensated by adjustment, and production costs may be reduced.

The position of the leaf drives may be adjusted by grouping, such that a group of leaf drives or even all of the leaf drives may be positioned at once. Therein, the leaf drives may form a unit, wherein the position and/or orientation of the unit may be adjustable. Alternatively, the position of single leaf drives or one or more groups of leaf drives may be adjustable. At least one of the leaf drives may fully or in part be adjustable such that the full leaf drive or at least one part thereof may be adjustable. As used herein, the expression "leaf drive" may refer to one or more elements adapted to position one or more of the leaves. Thus, each leaf drive may comprise the at least one segment disk with the at least one motor-side gear segment and the at least one leaf-side gear segment. Further, optionally, at least one pinion engaging the motor-side gear segment may form part of the leaf drive. Further, optionally, the at least one motor adapted to rotate the pinion may also form part of the leaf drive. Optionally, the gear rod-like drive engagement of the at least one leaf, which is adapted to interact with the leaf-side gear segment of the segment disk, may count as part of the leaf drive, too.

The adjustment and/or modification of the position of the leaf drives may be used to modify the engagement of the pivotable leaf-side gear segment into the gear rod-like drive engagement of the leaves. Thus, a slackness and/or backlash of the engagement may be adjusted or, preferably, reduced.

Similarly, additionally or alternatively to an adjustable mount of the position of the leaf drives, a relative position of the pinions and/or the motors with regard to the motor-side gear segments of the segment disks may be adjusted. The pinions and/or the motors may be mounted adjustably such that a relative position of the pinions with regard to the motor-side gear segments may be adjusted. Again, this positioning may be used to adjust or even reduce a slackness and/or backlash of the engagement of the pinions into the motor-side gear segments. By providing the adjustability, manufacturing may be simplified since manufacturing tolerances may be compensated by adjustment, and production costs may be reduced.

It has to be noted that the above-mentioned ideas of the adjustability of the pinions/motors, the adjustability of the leaf drive and the idea of the multi-part design of the motor bearings are realizable independently from the segmented design of the disks. Thus, these additional ideas may also be realized in other types of multi-leaf collimators.

Spacers may be provided between adjoining segment discs that reduce mutual friction to the largest extent.

Preferably, the leaves have a trapezoid cross section to the effect that they taper in the direction of a radiation source corresponding approximately to a divergence of beams. The sets of leaves may be tilted relative to an optical path to the effect that no rays can pass through a gap between the leaves.

Preferably, the leaf drives are designed in such a way that the leaves of the two sets of leaves can come in contact with each other with their front faces only outside of a center plane of the multi-leaf collimator.

In a further aspect of the present invention, which may be combined with the aspect disclosed above or which may be realized independently, a multi-leaf collimator for controlling a shape of a high-energy radiation beam emanating from a radiation source and propagating in a direction of propagation is disclosed, comprising:

a plurality of leaves individually displaceable in a direction of displacement that is generally transverse to the direction of propagation, said plurality of leaves having a predefined range of displacement (D) in said direction of displacement, each said leaf including a rack gear extending along the direction of displacement;

a plurality of individually rotatable segment disks positioned side by side along a common axis of rotation that is generally transverse to said direction of propagation and to said direction of displacement, each said segment disk corresponding to a respective one of said leaves, each said segment disk including a leaf-side gear segment formed along a first peripheral portion thereof that is engaged with said rack gear of the corresponding leaf to displace that leaf along said direction of displacement according to a motor-controlled rotation of said segment disk around said common axis of rotation; and a plurality of motor-driven pinions, each said motor-driven pinion being engaged with a respective one of said segment disks along a motor-side gear segment formed along a second peripheral portion thereof to provide said motor-controlled rotation thereof;

wherein the motor-side gear segments of any two adjacent segment disks are staggered in such a way that they will not abut each other throughout the range of displacement (D) of their corresponding leaves.

Preferably, each said motor-driven pinion is coupled to a distinct electrical motor to form a respective plurality of motor-pinion assemblies, wherein said plurality of motor-pinion assemblies are arranged in an arch-like pattern relative to said common axis of rotation of said plurality of segment disks. Said motor-pinion assemblies preferably are mounted on a common bearing block extending peripherally around said plurality of segment disks in an arch-like shape relative to said common axis of rotation, said motor-pinion assemblies being mounted on respective step-like gradations formed in said bearing block along the direction of said common axis of rotation for achieving respective engagement of said motor-driven pinions with said motor-side gear segments of said segment disks. Said motor-driven pinions preferably are wider than their associated motor-side gear segments in a direction of said common axis of rotation.

The multi-leaf collimator may further comprise at least one spacer disposed between each adjacent pair of said segment disks for reducing mutual friction therebetween.

Said plurality of leaves, said plurality of segment disks, and said plurality of motor-driven pinions collectively may form a first leaf/drive assembly, wherein the multi-leaf collimator further may comprise a second leaf/drive assembly generally similar to said first leaf/drive assembly and disposed on an opposing side of a center plane of the multi-leaf collimator.

Said plurality of leaves collectively may have a radiation source-facing side and a patient-facing side opposite said radiation source-facing side, wherein said plurality of segment disks may be disposed on said radiation source-facing side of said plurality of leaves, and wherein each of said plurality of segment disks may have a radius (R) along said first and second peripheral portions thereof that may sufficiently be comparable to said predefined range of displacement (D) of said leaves such that each said leaf may be fully displaced through its range of displacement (D) in less than one full turn of said segment disk, whereby structural compactness of the multi-leaf collimator may be facilitated. Said plurality of leaves in conjunction with said predefined range of displacement (D) may define an overall lateral range (L) in said direction of displacement, wherein said plurality of segment disks and said plurality of motor-pinion assemblies may be configured and dimensioned to be entirely confined within said overall lateral range (L) on said radiation source-facing side of said plurality of leaves. Said segment disk radius (R) preferably is greater than one-half of said predefined range of displacement (D) of said leaves. Said segment disk radius (R) preferably is greater than said predefined range of displacement (D) of said leaves.

Preferably, for each of said segment disks, said first peripheral portion thereof containing said leaf-side gear segment is non-overlapping with said second peripheral portion thereof containing said motor-side gear segment.

In a further aspect of the present invention which may be combined with one or both of the aspects disclosed above or which may be realized independently, a multi-leaf collimator is disclosed, for controlling a shape of a high-energy radiation beam emanating from a radiation source and propagating in a direction of propagation, comprising:

a plurality of leaves individually displaceable in a direction of displacement that is generally transverse to the direction of propagation, said plurality of leaves having a predefined range of displacement (D) in said direction of displacement, said plurality of leaves collectively having a radiation source-facing side and a patient-facing side opposite said radiation source-facing side, each said leaf including a rack gear extending along the direction of displacement;

a plurality of individually rotatable segment disks disposed on said radiation source-facing side of said plurality of leaves, said plurality of segment disks being positioned side by side along a common axis of rotation that is generally transverse to said direction of propagation and to said direction of displacement, each said segment disk corresponding to a respective one of said leaves, each said segment disk including a leaf-side gear segment formed along a first peripheral portion thereof that is engaged with said rack gear of the corresponding leaf to displace the corresponding leaf according to a motor-controlled rotation of said segment disk around said common axis of rotation; and a plurality of motor-driven pinions, each said motor-driven pinion being engaged with a respective one of said segment disks along a motor-side gear segment formed along a second peripheral portion thereof to provide said motor-controlled rotation thereof;

wherein each of said plurality of segment disks has a radius (R) along said first and second peripheral portions thereof that is sufficiently comparable to said predefined range of displacement of said leaves such that each said leaf can be fully displaced through its range of displacement (D) in less than one full turn of said segment disk;

whereby structural compactness of the multi-leave collimator is facilitated.

Preferably, each said motor-driven pinion is coupled to a distinct electrical motor to form a respective plurality of motor-pinion assemblies, wherein said plurality of motor-pinion assemblies are arranged in an arch-like pattern relative to said common axis of rotation of said plurality of segment disks. Said motor-pinion assemblies preferably are mounted on a common bearing block extending peripherally around said plurality of segment disks in an arch-like shape relative to said common axis of rotation, said motor-pinion assemblies being mounted on respective step-like gradations formed in said bearing block along the direction of said common axis of rotation for achieving respective engagement of said motor-driven pinions with said motor-side gear segments of said segment disks. Further preferably, said plurality of leaves in conjunction with said predefined range of displacement (D) may define an overall lateral range (L) in said direction of displacement, wherein said plurality of segment disks and said plurality of motor-pinion assemblies may be configured and dimensioned to be entirely confined within said overall lateral range (L) on said radiation source-facing side of said plurality of leaves.

Preferably, said segment disk radius (R) is greater than one-half of said predefined range of displacement (D) of said leaves. Said segment disk radius (R) may be greater than said predefined range of displacement (D) of said leaves.

The motor-side gear segments of any two adjacent segment disks preferably are staggered in such a way that there will be no angular overlap therebetween throughout the range of displacement (D) of their corresponding leaves. Said motor-driven pinions preferably are wider than their associated motor-side gear segments in a direction of said common axis of rotation.

The multi-leaf collimator may further comprise at least one spacer disposed between each adjacent pair of said segment disks for reducing mutual friction therebetween.

Said plurality of leaves, said plurality of segment disks, and said plurality of motor-driven pinions collectively preferably form a first leaf/drive assembly, wherein the multi-leaf collimator further may comprise a second leaf/drive assembly generally similar to said first leaf/drive assembly and disposed on an opposing side of a center plane of the multi-leaf collimator.

Preferably, for each of said segment disks, said first peripheral portion thereof containing said leaf-side gear segment is non-overlapping with said second peripheral portion thereof containing said motor-side gear segment.

For each of said segment disks, said first peripheral portion thereof containing said leaf-side gear segment preferably is non-overlapping with said second peripheral portion thereof containing said motor-side gear segment.

As disclosed above, the multi-leaf collimator may have a leaf-side pivotable gear segment located on a segment disc together with a motor-side gear segment engage with the gear rod-like drive engagement, with a pinion drivable by a motor engaging with the motor-side gear segment; by arranging the segment disks side by side for each set of leaves as a package on one axle; and by staggering the motor-side gear segments of two segment discs located next to each other in such a way that they will not abut each other.

The compactness of the multi-leaf collimator may further be achieved in accordance with one aspect of the invention by positioning the segment disks on a radiation source-facing side of the leaves, and sizing the segment disks to have a radius that is comparable in dimension to a predefined range of displacement of the leaves. By positioning the segment disks on the radiation source-facing side of the leaves (i.e., in the space "above" the leaves in the direction of the radiation source), the dimension of the multi-leaf collimator along the direction of displacement of the leaves (i.e., the "lateral" dimension of the multi-leaf collimator) may be kept to a minimum, and furthermore the vertical space between the radiation-shaping leaves and the patient can also advantageously be kept to a minimum. As a further advantage, the typically relatively large sizing of the segment disks may provide a relatively large circumference along which to position the driving pinions and their associated electrical motors, thereby allowing for a larger number of motorized pinion assemblies to be used, and therefore a larger number of individually controllable segments disks and their corresponding leaves to be accommodated.

The advantage of the multi-leaf collimator in accordance with the invention is that even in the case of extremely thin leaves, each leaf can be assigned a drive without any further ado. In this context it will be possible to arrange these drives in such a way that the drive mechanics and the motors do not project outwardly as seen from the leaves, thereby widening the collimator, but that they can be arranged close to the beam between the leaves and the radiation source. The drives may therefore be located in an interspace that typically is available in any event and where they are the least obtrusive, with the beam being able to exit the irradiation head—which typically essentially consists of the radiation source and the collimator—directly downstream of the opening formed by the leaves so that a position of the opening formed by the leaves for the beam exit will be possible very close to the patient.

Moreover, it will be possible to design the motors and the drive line in extremely space-saving, lightweight and compact fashion. The lightweight construction in turn has the advantage that the irradiation head will become lighter and can therefore be moved by a gantry or a robot arm into the various solid angle positions for the individual radiation applications extremely fast and precisely and without any extreme driving forces. This makes a faster move into different solid angle positions possible, thereby shortening the time intervals between the individual radiation applications and thus the treatment period of a patient. This is more pleasant for the latter because he or she needs to be fixed in a certain position for a shorter time. In addition, this will increase the cost effectiveness of the irradiation device.

The fact that the motor-side gear segments of two adjacent segment disks may be staggered in such a way that they will not abut each other may serve to prevent an engagement of a pinion with a gear segment not assigned to it even if component measurements or component positions are not exact due to production tolerances. In this way, the tolerance parameters may be kept within an economically justifiable range.

The aforementioned measure also may facilitate the advantageous further development of making the pinions wider than the motor-side gear segments. This may reduce, on the one hand, the tolerance requirements of the pinion positioning in relation to the motor-side gear segments even further and, on the other hand, may make it possible to design the leaves with their gear segments extremely thin without the possibility of thereby losing the pinion engagement with the gear segments as a consequence of tolerance deviations.

As outlined above, another advantageous and preferred embodiment provides for the motors for each package of segment discs to be arranged strung together in an arch-shaped sequence within the engagement range of the respective gear segments. This makes it possible to string together a great number of motors almost with no distance in between and to house them in the smallest possible space. In this case, the motors are preferably mounted on a bearing block that encompasses one package of segment discs each in their circumferential area.

A particularly clear arrangement can be achieved by providing a step-like gradation of the pinions driven by the motors for their engagement with the various gear segments. If such a step-like gradation is provided in the bearing block, motors with driven pinions of the same type of construction may be provided, i.e. of the same axle arrangement and pinion positioning, and the step-like gradation may set the parameters for the positioning relative to the assigned gear segments.

A further development provides that at least two step-like gradations of the aforementioned kind may be provided, with segment discs located next to each other being driven by motors with pinions assigned to various of these step-like gradations and the motor-side gear segments of adjacent segment discs being located in various areas of the circumference of the package of segment discs. For example, in the case of two step-like gradations, the motors can be arranged relative to the segment discs in alternating fashion in such a way that in the sequence of the segment discs, one motor is always assigned to one step-like gradation and one motor to the other in alternating fashion. This may then make it possible to arrange the motor-side gear segments of adjacent segment discs in different areas of the circumference of the package of segment discs. Since in this way motor-side gear segments will never be arranged directly next to each other, not even in partial areas, a pinion may protrude laterally beyond the gear segments without being able to engage erroneously with a gear segment of the adjacent segment disc at any time. This makes it possible to provide pinion protrusions relative to the gear segments so that the pinions jut into the area of the nearest segment disc without coming into contact with it.

For example, in the case of two step-like gradations, the pinions of a first gradation may be assigned to the 1st, 3rd, 5th, 7th, etc. segment disc and the pinions of a second gradation to the 2nd, 4th, 6th, 8th, etc. segment disc. In that case, the motor-side gear segments of the 1st, 3rd, 5th, 7th, etc. segment disc are arranged in a different circumferential area of the package of segment discs than the motor-side gear segments of the 2nd, 4th, 6th, 8th, etc. segment disc. Thus, for example, the gear segment of the 2nd segment disc has neither an abutting gear segment of the 1st segment disc nor a gear segment of the adjacent 3rd segment disc, making it possible for the pinion interacting with the 2nd segment disc to protrude on both sides without touching the 1st and 3rd segment discs during a positioning movement. This applies correspondingly to all segment discs of the entire package of segment discs. This principle could of course also be realized with three or more of such step-like gradations.

Moreover, in the case of the gear rod-like drive engagement of the leaves, collisions caused by tolerance deviations or positioning errors can be avoided by designing the width of the gear rod-like drive engagement of the leaves different than the width of the leaf-side gear segment that interacts with it. The practical implementation may occur in two different ways, either in such a way that the gear rod-like drive engagement of the leaves is wider than the leaf-side gear segment so that it can only engage with this drive engagement.

Another design option preferably provides for the gear rod-like drive engagement of the leaves to be designed narrower in this area through a tapering of the leaf, thereby making the leaf-side gear segment wider than the gear rod-like drive engagement of the leaves. In this way, the leaf-side gear segment can only engage with the gear rod-like drive engagement of this leaf because, due to the tapering of the drive engagements of the adjacent leaves, an engagement of the gear segment with the adjacent gear rod-like formations will not be possible if the tolerance deviation does not exceed the degree of these taperings, which, however, is not a very great requirement.

One possibility of increasing the number of the compactly arranged motors consists of equipping the optional bearing block with motors on both sides. In this context, on both sides means that the motors protrude in opposite directions away from the leaves, with the axles bearing the pinions being arranged between motor and bearing block where their engagement area is.

An even more dense arrangement of the motors preferably can be achieved by arranging the motors above each other in an arch-shaped sequence through the arrangement of motor-side gear segments on corresponding differing radii of the segment discs. In the practical execution, for example, one package of segment discs has the motor-side gear segments with greater radii in an interior area of the package and the motor-side gear segment with smaller radii in an area closer to the exterior. According to such an arrangement principle, two or, in corresponding fashion several, arch-shaped arrangements of motors can be arranged on top of each other on differing radii. These differing radii which, after all, also may effect different transmission ratios should of course be actuated accordingly by a control device in order to initiate the required leaf positions. If the leaf-side gear segments are also located on smaller radii, the gear rod-like drive engagements of the leaves would, of course, have to be increased accordingly so that this engagement can take place. However, this would not be required since the segment discs, after all, execute only pivoting movements in the engagement area of the gear segments so that a segment disc may also have gear segments located on differing radii. Differing axle positions of the segment discs are conceivable as well, as are internal gear teeth systems of doughnut-shaped segment discs.

It is advantageously provided for the bearing block to position the pinions directly or indirectly by means of positioning agents in their engagement positions relative to the motor-side gear segments. Directly means, for example, that the pinions are directly positioned at a stopper surface of the bearing block. Indirectly means that the pinions are moved into position at the bearing block via the positioning of some retaining element. The latter could, for example, be done by attaching the pinions on axles that are mounted in a preset manner in motor bearings, with the latter being accordingly positioned and attached on the bearing block. The preferred step-like gradations of the arrangement of motors mentioned above can be achieved, for example, by equipping the at least one bearing block with step-like gradations of accommodations for motor bearings so that in this way, the bearing block may position the pinions indirectly with the aid of the motor bearings.

Since the segment discs may execute differing movements, e.g. depending on what position the appurtenant leaf is moved into, they must be freely movable and may not show, if at all possible, any significant mutual friction. It is therefore generally proposed for this embodiment or other embodiments to optionally arrange a spacer between adjacent segment discs.

Preferably, the multi-leaf collimator will be designed in such a way that the leaves will have a trapeze-shaped cross section to the effect that they preferably will taper in the direction of the radiation source, approximately following the divergence of the beams. The reason is that the beams used are so strong that the leaves must have a not insignificant strength to be shielded against the radiation in the direction of the beam. As a rule, this amounts to several centimeters. Therefore, the delimitations of the openings for the beam exit should, if at all possible, run in the direction of the beam so as not to create a penumbra which is created when no complete shielding is available for the beam exit opening formed by the leaves due to delimitations not running in the direction of the beam.

The leaves of such a multi-leaf collimator preferably are crafted in such a way that they will lie closely on top of each other, preferably at least nearly without any gap. In practice, however, it can not be avoided that tiniest rays will still pass through the gaps of leaves due to surface irregularities even if, as a rule, they lie only within the micrometer range such as below 500 µm, preferably below 200 µm and more preferably below 100 µm or even below 50 µm, below 10 µm or below 5 µm. This may be prevented by tilting the sets of leaves tilted relative to the path of rays in such a way that no ray will be able to pass through the course of the gap no longer aligned in the direction of the beam. Since the gap typically is within the range of a few micrometers, such a tilting may be so minor that it does not run counter to the above-mentioned prevention of the creation of a relevant penumbra. For a tilting moving within the micrometer range typically can not lead to the creation of a significant penumbra.

If leaves of two sets of leaves are made to completely contact each other with their front faces because the beam is supposed to be completely shielded in this area, radiation may in some cases of course penetrate there through a gap formed by front faces of the leaves. For this reason it is proposed that the leaf drives may be designed in such a way that leaves of the two sets of leaves will be able to touch each other with their front faces only outside of a center plane of the multi-leaf collimator. In this way, the gap in the area of the abutting front faces of leaves may be removed from the center plane in such a way that it will also have a different course than the course of rays. Since this gap, too, is only within the range of a few micrometers, it will suffice if the front faces touch each other in the range of a few tenths or of a few millimeters outside of the center plane.

Summarizing the above-mentioned ideas, the following embodiments of the present invention are specifically preferred:

Embodiment 1: Multi-leaf collimator with leaf drives, with two sets of displaceable leaves arranged side by side of each other and facing each other in order to impress a high-energy beam with the shape of an irregularly formed treatment object by enabling each of the leaves to assume a position oriented along the shape of the treatment object by means of the leaf drives, with the leaf drives being designed in such a way that the leaves are each equipped with a gear rod-like drive engagement in a direction of displacement, wherein a pivotable leaf-side gear segment located, together with a motor-side gear segment on a segment disk, engages with the gear rod-like drive engagement, with a pinion drivable by a motor engaging with the motor-side gear segment, wherein the segment disks are arranged side by side for each set of leaves as a package on one axle, and wherein the motor-side gear segments of two segment disks located next to each other are staggered in such a way that they will not abut each other.

Embodiment 2: Multi-leaf collimator in accordance with Embodiment 1, wherein the pinions are wider than the motor-side gear segments.

Embodiment 3: Multi-leaf collimator in accordance with Embodiments 1 or 2, wherein the motors for each package of segment discs in an engagement range of the respective motor-side gear segments are arranged in series in the shape of an arch.

Embodiment 4: Multi-leaf collimator in accordance with Embodiment 3, wherein the motors are mounted on a bearing block which encompasses in each case a package of segment discs in their circumferential range.

Embodiment 5: Multi-leaf collimator in accordance with Embodiment 3 or 4, wherein a step-like gradation of an arrangement of the pinions driven by the motors is provided for their engagement with the various motor-side gear segments.

Embodiment 6: Multi-leaf collimator in accordance with Embodiment 5, wherein at least two step-like gradations are provided, with segment discs located next to each other being driven by motors with pinions assigned to various ones of these step-like gradations and the motor-side gear segments of segment discs lying next to each other being located in different areas of the circumference of the package of segment discs.

Embodiment 7: Multi-leaf collimator in accordance with one of Embodiments 1 through 6, wherein, relative to its width, the gear rod-like drive engagement of the leaves is designed differently from the width of the leaf-side gear segment.

Embodiment 8: Multi-leaf collimator in accordance with one of Embodiments 4 through 6, wherein the bearing block is equipped on both sides with motors.

Embodiment 9: Multi-leaf collimator in accordance with Embodiments 3 through 8, wherein due to an arrangement of motor-side gear segments on corresponding varying radii of the segment discs, the motors are arranged in arch-shaped sequences, preferably lying on top of each other.

Embodiment 10: Multi-leaf collimator in accordance with one of Embodiments 4 through 9, wherein the bearing block positions the pinions indirectly or directly by means of positioning agents in their engagement position opposite the motor-side gear segments.

Embodiment 11: Multi-leaf collimator in accordance with Embodiment 10, wherein the pinions are mounted on axles supported by motor bearings and the latter are mounted on the bearing block.

Embodiment 12: Multi-leaf collimator in accordance with Embodiment 11, wherein the motor bearings each comprise a motor holder for mounting the motor and an axle bearing for bearing the axle.

Embodiment 13: Multi-leaf collimator in accordance with Embodiment 12, wherein the motor holders are made of aluminum and the axle bearings are made of bronze.

Embodiment 14: Multi-leaf collimator in accordance with one of Embodiments 1 through 13, wherein the leaf drives are mounted adjustably such that a position of the leaf drives relative to the leaves may be adjusted.

Embodiments 15: Multi-leaf collimator in accordance with Embodiment 14, wherein the position of the leaf drives is adjustable by at least one excenter.

Embodiment 16: Multi-leaf collimator in accordance with one of Embodiments 1 through 15, wherein spacers are provided between adjoining segment discs that reduce mutual friction to the largest extent.

Embodiment 17: Multi-leaf collimator in accordance with one of Embodiments 1 through 16, wherein the leaves have a trapezoid cross section to the effect that they taper in the direction of a radiation source corresponding approximately to a divergence of the high-energy beam.

Embodiment 18: Multi-leaf collimator in accordance with Embodiment 17, wherein the sets of leaves are tilted relative to an optical path to the effect that no rays can pass through a gap between the leaves.

Embodiment 19: Multi-leaf collimator in accordance with one of Embodiments 1 through 18, wherein the leaf drives are designed in such a way that the leaves of the two sets of leaves can come in contact with each other with their front faces only outside of a center plane of the multi-leaf collimator.

Embodiment 20: Multi-leaf collimator in accordance with one of Embodiments 1 through 19, wherein the pinions and/or the motors are mounted adjustably such that the relative position of the pinions with regard to the motor-side gear segments may be adjusted.

Embodiment 21: A multi-leaf collimator (MLC) for controlling a shape of a high-energy radiation beam emanating from a radiation source and propagating in a direction of propagation, comprising:

a plurality of leaves individually displaceable in a direction of displacement that is generally transverse to the direction of propagation, said plurality of leaves having a predefined range of displacement in said direction of displacement, each said leaf including a rack gear extending along the direction of displacement;

a plurality of individually rotatable segment disks positioned side by side along a common axis of rotation that is generally transverse to said direction of propagation and to said direction of displacement, each said segment disk corresponding to a respective one of said leaves, each said segment disk including a leaf-side gear segment formed along a first peripheral portion thereof that is engaged with said rack gear of the corresponding leaf to displace that leaf along said direction of displacement according to a motor-controlled rotation of said segment disk around said common axis of rotation; and a plurality of motor-driven pinions, each said motor-driven pinion being engaged with a respective one of said segment disks along a motor-side gear segment formed along a second peripheral portion thereof to provide said motor-controlled rotation thereof;

wherein the motor-side gear segments of any two adjacent segment disks are staggered in such a way that they will not abut each other throughout the range of displacement (D) of their corresponding leaves.

Embodiment 22: The MLC of Embodiment 21, each said motor-driven pinion being coupled to a distinct electrical motor to form a respective plurality of motor-pinion assemblies, wherein said plurality of motor-pinion assemblies are arranged in an arch-like pattern relative to said common axis of rotation of said plurality of segment disks.

Embodiment 23: The MLC of Embodiment 22, wherein said motor-pinion assemblies are mounted on a common bearing block extending peripherally around said plurality of segment disks in an arch-like shape relative to said common axis of rotation, said motor-pinion assemblies being mounted on respective step-like gradations formed in said bearing block along the direction of said common axis of rotation for achieving respective engagement of said motor-driven pinions with said motor-side gear segments of said segment disks.

Embodiment 24: The MLC of Embodiment 21, wherein said motor-driven pinions are wider than their associated motor-side gear segments in a direction of said common axis of rotation.

Embodiment 25: The MLC of Embodiment 24, further comprising a spacer agent disposed between each adjacent pair of said segment disks for reducing mutual friction therebetween.

Embodiment 26: The MLC of Embodiment 21, said plurality of leaves, said plurality of segment disks, and said plurality of motor-driven pinions collectively forming a first leaf/drive assembly, wherein the MLC further comprises a second leaf/drive assembly generally similar to said first leaf-drive assembly and disposed on an opposing side of a center plane of the MLC.

Embodiment 27: The MLC of Embodiment 21, said plurality of leaves collectively having a radiation source-facing side and a patient-facing side opposite said radiation source-facing side, wherein said plurality of segment disks are disposed on said radiation source-facing side of said plurality of leaves, and wherein each of said plurality of segment disks has a radius (R) along said first and second peripheral portions thereof that is sufficiently comparable to said predefined range of displacement of said leaves such that each said leaf can be fully displaced through its range of displacement (D) in less than one full turn of said segment disk, whereby structural compactness of the MLC is facilitated.

Embodiment 28: The MLC of Embodiment 27, said plurality of leaves in conjunction with said predefined range of displacement (D) defining an overall lateral range (L) in said direction of displacement, wherein said plurality of segment disks and said plurality of motor-pinion assemblies are configured and dimensioned to be entirely confined within said overall lateral range (L) on said radiation source-facing side of said plurality of leaves.

Embodiment 29: The MLC of Embodiment 28, wherein said segment disk radius (R) is greater than one-half of said predefined range of displacement (D) of said leaves.

Embodiment 30: The MLC of Embodiment 29, wherein said segment disk radius (R) is greater than said predefined range of displacement (D) of said leaves.

Embodiment 31: The MLC of Embodiment 21, wherein, for each of said segment disks, said first peripheral portion thereof containing said leaf-side gear segment is non-overlapping with said second peripheral portion thereof containing said motor-side gear segment.

Embodiment 32: A multi-leaf collimator (MLC) for controlling a shape of a high-energy radiation beam emanating from a radiation source and propagating in a direction of propagation, comprising:

a plurality of leaves individually displaceable in a direction of displacement that is generally transverse to the direction of propagation, said plurality of leaves having a predefined range of displacement (D) in said direction of displacement, said plurality of leaves collectively having a radiation source-facing side and a patient-facing side opposite said radiation source-facing side, each said leaf including a rack gear extending along the direction of displacement;

a plurality of individually rotatable segment disks disposed on said radiation source-facing side of said plurality of leaves, said plurality of segment disks being positioned side by side along a common axis of rotation that is generally transverse to said direction of propagation and to said direction of displacement, each said segment disk corresponding to a respective one of said leaves, each said segment disk including a leaf-side gear segment formed along a first peripheral portion thereof that is engaged with said rack gear of the corresponding leaf to displace the corresponding leaf according to a motor-controlled rotation of said segment disk around said common axis of rotation; and a plurality of motor-driven pinions, each said motor-driven pinion being engaged with a respective one of said segment disks along a motor-side gear segment formed along a second peripheral portion thereof to provide said motor-controlled rotation thereof;

wherein each of said plurality of segment disks has a radius (R) along said first and second peripheral portions thereof that is sufficiently comparable to said predefined range of displacement (D) of said leaves such that each said leaf can be fully displaced through its range of displacement (D) in less than one full turn of said segment disk;

whereby structural compactness of the MLC is facilitated.

Embodiment 33: The MLC of Embodiment 32, each said motor-driven pinion being coupled to a distinct electrical motor to form a respective plurality of motor-pinion assemblies, wherein said plurality of motor-pinion assemblies are arranged in an arch-like pattern relative to said common axis of rotation of said plurality of segment disks.

Embodiment 34: The MLC of Embodiment 33, wherein said motor-pinion assemblies are mounted on a common bearing block extending peripherally around said plurality of segment disks in an arch-like shape relative to said common axis of rotation, said motor-pinion assemblies being mounted on respective step-like gradations formed in said bearing block along the direction of said common axis of rotation for achieving respective engagement of said motor-driven pinions with said motor-side gear segments of said segment disks.

Embodiment 35: The MLC of Embodiment 33, said plurality of leaves in conjunction with said predefined range of displacement (D) defining an overall lateral range (L) in said direction of displacement, wherein said plurality of segment disks and said plurality of motor-pinion assemblies are configured and dimensioned to be entirely confined within said overall lateral range (L) on said radiation source-facing side of said plurality of leaves.

Embodiment 36: The MLC of Embodiment 32, wherein said segment disk radius (R) is greater than one-half of said predefined range of displacement (D) of said leaves.

Embodiment 37: The MLC of Embodiment 36, wherein said segment disk radius (R) is greater than said predefined range of displacement (D) of said leaves.

Embodiment 38: The MLC of Embodiment 32, wherein the motor-side gear segments of any two adjacent segment disks are staggered in such a way that there will be no angular overlap therebetween throughout the range of displacement (D) of their corresponding leaves.

Embodiment 39: The MLC of Embodiment 38, wherein said motor-driven pinions are wider than their associated motor-side gear segments in a direction of said common axis of rotation.

Embodiment 40: The MLC of Embodiment 39, further comprising a spacer agent disposed between each adjacent pair of said segment disks for reducing mutual friction therebetween.

Embodiment 41: The MLC of Embodiment 32, said plurality of leaves, said plurality of segment disks, and said plurality of motor-driven pinions collectively forming a first leaf/drive assembly, wherein the MLC further comprises a second leaf/drive assembly generally similar to said first leaf-drive assembly and disposed on an opposing side of a center plane of the MLC.

Embodiment 42: The MLC of Embodiment 32, wherein, for each of said segment disks, said first peripheral portion thereof containing said leaf-side gear segment is non-overlapping with said second peripheral portion thereof containing said motor-side gear segment.

BRIEF DESCRIPTION OF THE DRAWINGS

In the following, the invention will be explained by way of schematic diagrams and views of exemplary embodiments. In the figures, identical reference numbers refer to identical components or components having the same or similar functions. The exemplary embodiments are given for illustrative purposes, and the invention is not restricted to these embodiments.

Shown are in

FIG. 1 a sketch of the principle of a multi-leaf collimator in a top view,

FIG. 2 a sketch of the principle of a multi-leaf collimator in a cut view,

DETAILED DESCRIPTION

Figure 3:
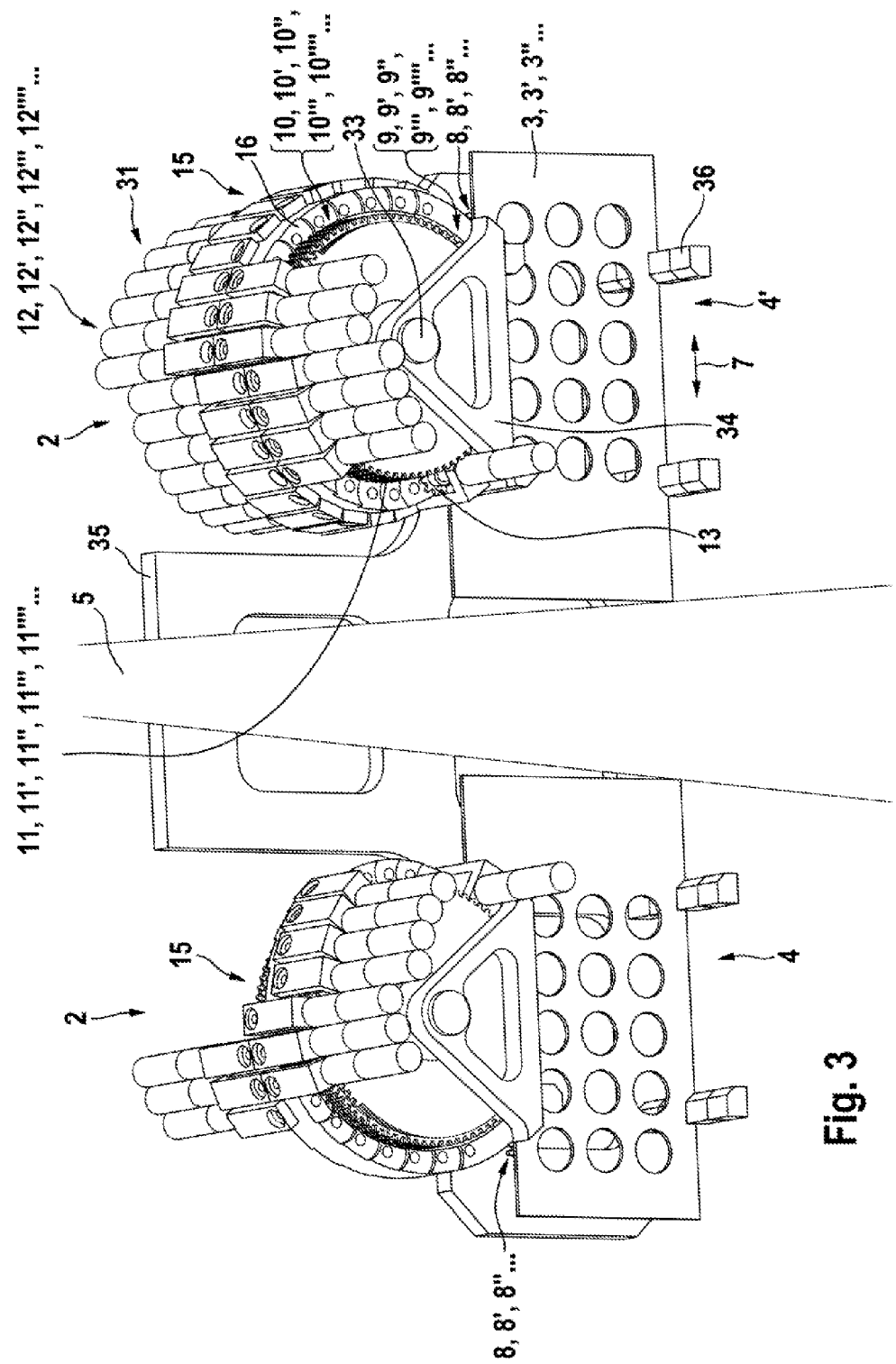
FIG. 3 a leaf drive in accordance with the invention to describe the functional principle, FIG. 4 a fragmented representation of components of the leaf drive for an explanation of the principle in accordance with the invention, FIG. 5 a leaf drive in accordance with the invention installed into a base frame, FIG. 6 a bearing block for an arrangement of motors and pinions, FIG. 7 a motor bearing FIG. 8 an installation of a motor bearing into a bearing block, FIG. 9 a schematic diagram of two arch-shaped arrangements of motors lying above each other, FIGS. 10A-10B a conceptual side view of an exemplary segment disk, motor-driven pinion, and leaf when the leaf is at the two most extreme positions along the direction of displacement, FIGS. 11A-11C a conceptual side view of two adjacent segment disks, and their correspondingly adjacent motor-driven pinions and leaves, when the adjacent leaves are at different combinations of extreme positions along the direction of displacement and FIGS. 12A-12C several perspective partial representations of a further embodiment of a leaf drive.

FIG. 1 shows a schematic diagram of a multi-leaf collimator 1 in a top view. A multi-leaf collimator 1 consists of two sets 4, 4' of leaves 3, 3', 3" . . . that are displaceable in the direction of the double arrow 7. In this way it will be possible to impress the re-created shape 6' of a treatment object 6 (see FIG. 2) upon a high-energy beam 5 (see FIG. 2). In this case, the leaves 3, 3', 3" . . . may be brought together as shown in FIG. 1 by way of leaves moved together 3B, or they remain moved apart to create the re-created shape 6' of the treatment object 6 as shown in FIG. 1 by way of leaves separated 3A. When the leaves 3, 3', 3" . . . are moved together, their front faces 29 touch each other but not in a center plane 30 of the multi-leaf collimator 1 but somewhat offset so that a gap 27 created between two front faces 29 preferably will not lead to a beam being able to pass through this gap 27. In the case of such an offset relative to the center plane 30, the gap 27 has a different alignment than the course of the high-energy beams 5 and a beam can not pass through. However, the leaves 3, 3', 3" . . . preferably are crafted so precisely that such a gap 27 typically will lie within the range of a few tenths or hundredths of a millimeter.

FIG. 2 shows a diagram of the principle of a multi-leaf collimator 1 in a cut view. Here, a radiation source 25 is represented, starting from which the high-energy beam 5 collides with the multi-leaf collimator 1, thereby receiving the re-created shape 6' of a treatment object 6. This re-created shape 6' typically should of necessity be smaller than the treatment object 6, corresponding to the divergence of the high-energy beam 5, so that it can be hit with great accuracy by the high-energy beam 5 without adjacent tissues being irradiated. An irradiation head 38 is drawn schematically, showing that a free structural space 39 is available for leaf drives 2 between the radiation source 25 and the multi-leaf collimator 1 on both sides of the high-energy beam 5.

FIG. 2 also shows that the leaves 3, 3', 3" . . . may have a trapeze-shaped cross section so that a course of the lateral delimitations of the leaves 3, 3', 3" . . . is created that corresponds to the course of the high-energy beam 5. In this way, the creation of a penumbra may be avoided that typically would occur in the case of rectangular leaves since then, an area of partial shielding of the high-energy beam 5—that is, not provided by the entire thickness of the material of the leaves 3, 3', 3" . . . —would be created.

However, there is also the problem here that between the individual leaves 3, 3', 3" . . . , the gaps 27 may be created at their lateral delimitations, thereby creating radiation leaks in the shielding area. This is avoided by slightly tilting the multi-leaf collimator 1 relative to the course of the high-energy beam 5. This means that a center 28 at which imaginary continuations of the leaf delimitations converge may be slightly offset relative to the radiation source 25. This is depicted here in greatly exaggerated form for the purpose of visualization. Since the gap 27 typically lies within the range of a few hundredths of a millimeter, a distance of the center 28 at which imaginary continuations of the leaf delimitations converge from the radiation source 25 within the range of a few tenths of a millimeter typically will suffice to prevent a significant recurrence of the penumbra avoided by means of the aforementioned measure. In this case, the representation of the irradiation head 38 may be reduced by a multiple relative to its actual size.

FIG. 3 shows a leaf drive 2 in accordance with the invention and a base frame 35 for a description of the functional principle. In the representation of FIG. 3, parts of the leaf drive 2 and of the base frame 35 have been omitted so as not to overload the drawing and to leave essential parts visible. Since a set 4, 4' of leaves 3, 3', 3" . . . is located on either side of the high-energy beam 5, a drive unit of the leaf drive 2 should be arranged on either side of the high-energy beam 5 as well. However, of the leaves 3, 3', 3" . . . , only one is represented symbolically; the number of leaves 3, 3', 3" . . . for each set 4, 4' typically should lie within a range that lies within a magnitude of 30 to 100. Preferably all of the leaves 3, 3', 3" . . . are mounted by means of guiding devices 36 and are driven by the leaf drive 2.

Figure 5:
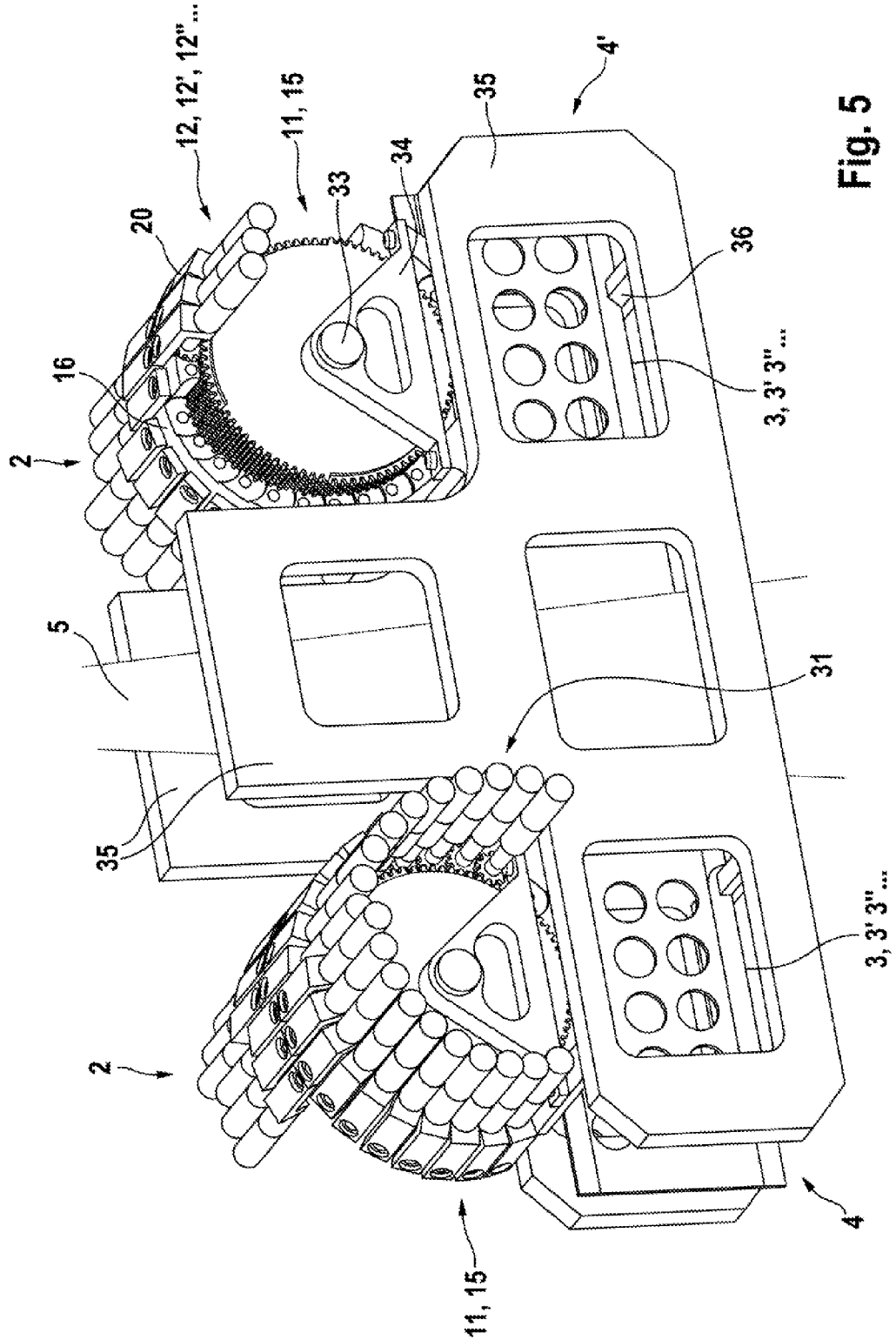

The leaf drive 2 in accordance with the invention may consist of two packages 15 of segment discs 11, 11', 11", . . . , with their number preferably corresponding to the number of leaves 3, 3', 3" . . . of a set 4, 4' of leaves, thus preferably within the magnitude indicated above. The segment discs 11, 11', 11", . . . of a package 15 of segment discs 11, 11', 11", . . . are mounted on an axle 33 which in turn is attached to the base frame 35 by means of at least one bearing block 34. The base frame 35 is shown in FIG. 5. Preferably, each segment disc 11, 11', 11", . . . bears a leaf-side gear segment 9, 9', 9", . . . that interacts with a gear rod-like drive engagement 8, 8', 8" . . . (also called rack gear) of a leaf 3, 3', 3" . . . as well as, in a different circumferential area, a motor-side gear segment 10, 10', 10", . . . , with which a pinion 13, 13', 13" driven by a motor 12, 12', 12", . . . engages in order to drive the respective segment disc 11, 11', 11", . . . so that the respective leaf 3, 3', 3" . . . can be moved into the desired position. This is indicated by the double arrow 7 (displacement direction of the leaf) below the symbolically represented leaf 3, 3', 3" . . . .

Preferably, the motors 12, 12', 12", . . . are kept in their position by means of a bearing block 16 which preferably is also arranged on the base frame 35 so that an arch-shaped sequence 31 of motors 12, 12', 12", . . . may be created along the engagement range of the pinions 13, 13', 13", . . . . As illustrated, more motors 12, 12', 12", . . . can be accommodated by equipping the bearing block 16 on both sides with protruding motors 12, 12', 12", . . . .

From the representation of FIG. 3 it can also be seen how the arrangement of the leaf drives 2 above the leaves 3, 3', 3" . . . is possible, thereby allowing the use of a free structural space 39 (see FIG. 2) between the leaves 3, 3', 3" . . . of the multi-leaf collimator 1 and the radiation source 25. This is a great advantage of the invention since the irradiation head 38 (see FIG. 2) in which the multi-leaf collimator 1 and the radiation source 25 preferably are arranged does not need to be designed wider because of the leaf drive 2 nor is the space below the leaves 3, 3', 3" . . . obstructed by drive elements, allowing the multi-leaf collimator 1 to be moved very close to the treatment object 6.

Figure 4:
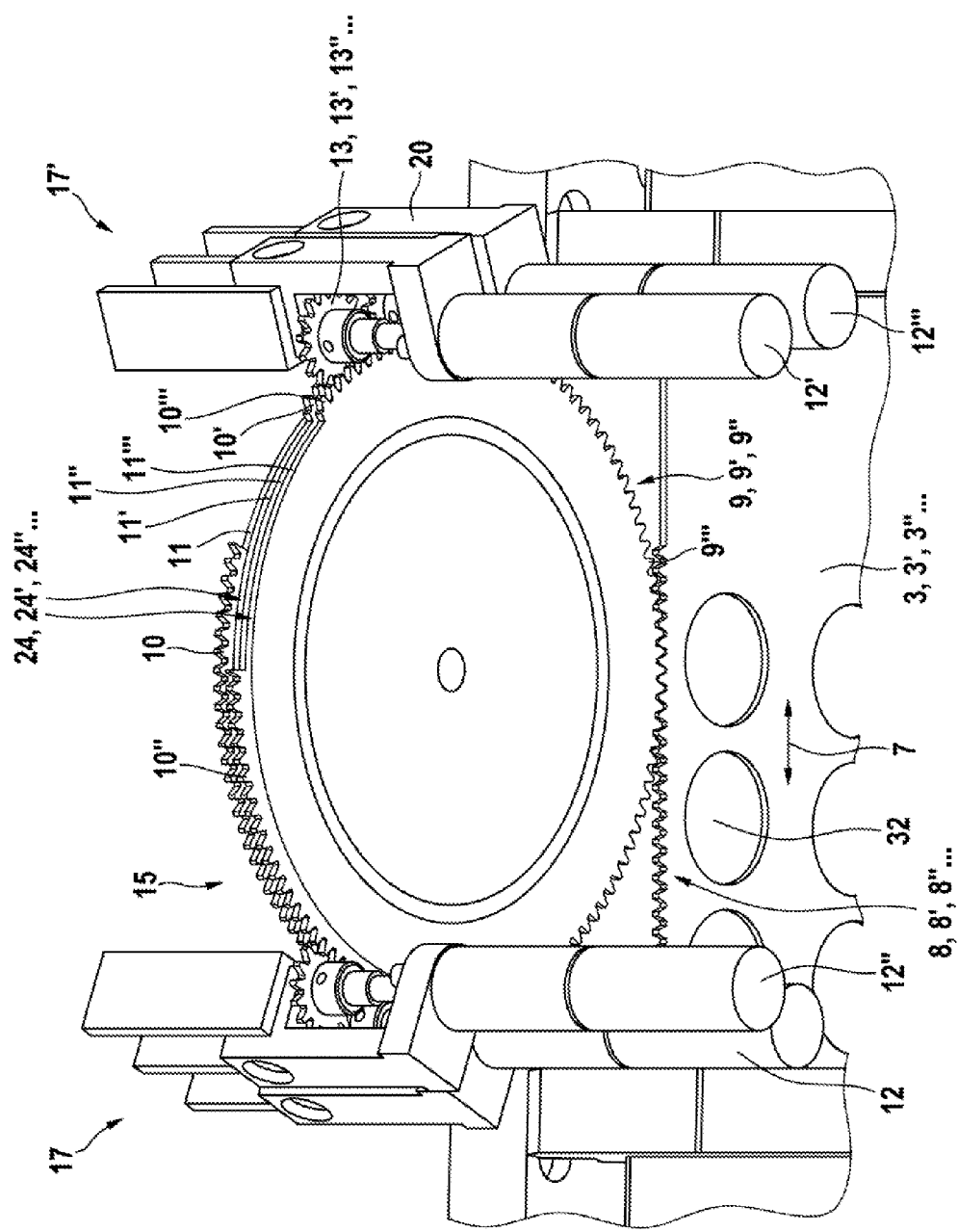

FIG. 4 shows a fragmented representation of components of a leaf drive 2 to explain the principle of the invention. For an explanation of the principle, only a part of the segment discs 11, 11', 11", . . . of a package 15 of segment discs 11, 11', 11", . . . is shown here. Also, only one leaf 3, 3', 3" . . . is represented symbolically which represents all leaves 3, 3', 3" . . . that may be positioned by means of the leaf drive 2 in the manner described before. The purpose of this representation is the description of an advantageous further embodiment of the invention which consists of a suitable allocation of motors 12, 12', 12", . . . with pinions 13, 13', 13" . . . to the motor-side gear segments 10, 10', 10", . . . .

To assure that the pinions 13, 13', 13", . . . driven by the motors 12, 12', 12", . . . , the pinions 13, 13', 13", . . . should be staggered in such a way that each pinion 13, 13', 13", . . . is allocated to a motor-side gear segment 10, 10', 10", . . . of the segment discs 11, 11', 11", . . . . This staggered arrangement of pinions 13, 13', 13" . . . may be carried out in two gradations 17, 17' in the following manner:

In the case of the package 15 of segment discs 11, 11', 11", . . . , the motor-side gear segments 10, 10', 10", . . . may be arranged in two different circumferential areas in such a way that the alternating arrangement will not lead to any directly adjacent motor-side gear segments 10, 10', 10", . . . .

In FIG. 4, one segment disc 11 has a motor-side gear segment 10 that extends into the area of the left half of the illustration. The motor-side gear segment 10' of the adjacent segment disc 11' is offset in such a way that it will not abut the gear segment 10 but instead extend into the right half of the illustration. Only the subsequent segment disc 11" has a motor-side gear segment 10" that may be located in the same circumferential area of the package 15 of segment discs 11, 11', 11", . . . as the first motor-side gear segment 10, and so forth. Thus, there may be a distance between these two motor-side gear segments 10 and 10" that approximately may correspond to the width of the intermediary segment disc 11'. However, this distance may be larger by a minor amount since spacers 24, 24', 24" . . . may be arranged between all segment discs 11, 11', 11", . . . in order to preferably prevent any friction between adjacent segment discs 11, 11', 11", . . . .

In a corresponding manner, on the other side, i.e. the right half of the illustration, the motor-side gear segment 10' of the segment disc 11' may not followed by the subsequent motor-side gear segment 10" since it may be located in the left half of the picture but by the motor-side gear segment 10' of the segment disc 11" to the effect that a distance between gear segments 10' and 10'" exists here as well.

For the engagement with the respective motor-side gear segments 10, 10", . . . on the one side and of the motor-side gear segments 10', 10''', . . . on the other side, the allocated motors 12, 12", . . . as well as 12', 12''', . . . may be arranged in the at least two gradations 17 and 17' on each side. Such an arrangement can be achieved, for example, by means of the bearing block 16 as described earlier in FIG. 3.

The purpose of this designs lies in the fact that the pinions 13, 13', 13", . . . may be somewhat wider than the allocated motor-side gear segments 10, 10', 10", . . . , preferably without any engagement with a gear segment 10, 10', 10", . . . of the adjacent segment disc 11, 11', 11", . . . being possible.

Each segment disc 11, 11', 11", . . . preferably has a leaf-side gear segment 9, 9', 9", . . . on the underside of the segment discs 11, 11', 11", . . . . They engage with gear rod-like drive engagements 8, 8', 8", . . . of the leaves 3, 3', 3", . . . . In this case, an erroneous engagement with the gear rod-like drive engagement 8, 8', 8", . . . of an adjacent leaf 3, 3', 3", . . . may be avoided by the fact that the leaf-side gear segments 9, 9', 9", . . . may be somewhat tapered relative to the thickness of the segment discs. Conversely, of course, the respective gear rod-like drive engagement 8, 8', 8" . . . may be somewhat tapered relative to the thickness of a leaf 3, 3', 3" . . . so that an engagement of a leaf-side gear segment 9, 9', 9", . . . with a gear rod-like drive engagement 8, 8', 8" . . . not allocated to it preferably may not occur.

With regard to the leaves 3, 3', 3" . . . , it can also be seen that outside of their shielding range they may have punched out holes 32, preferably through holes, that may serve to reduce their weight. This area may overlap with the area in which the gear rod-like drive engagement 8, 8', 8", . . . is located.

The motors 12, 12', 12''' . . . may be mounted on motor bearings 20 than can be attached for example to the at least one optional bearing block 16.

This representation, as mentioned before, is fragmentary in order to describe the principle. In reality, a great number of leaves 3, 3', 3", . . . per set 4 or, respectively, 4' of leaves may be arranged in the described manner, with the leaves 3, 3', 3", . . . being driven in the corresponding manner by means of segment discs 11, 11', 11", . . . .

FIG. 5 shows an embodiment of a leaf drive 2 in accordance with the invention that is installed into the base frame 35. The bearing blocks 34 for the axles 33 on which the segment discs 11, 11', 11", . . . are mounted are attached to this base frame 35. The bearing blocks 34 may be attached to this base frame 35 as well. They bear the motors 12, 12', 12", . . . with the aid of the motor bearings 20 and position the pinions 13, 13', 13", . . . in their engagement position. Since in this representation the motors 12, 12', 12", . . . protruding forward are completely drawn in, the arch-shaped sequence 31 of the motors 12, 12', 12", . . . is well visible. This clearly shows how the motors 12, 12', 12", . . . may be densely packed and arranged in neat fashion.

Figure 6:
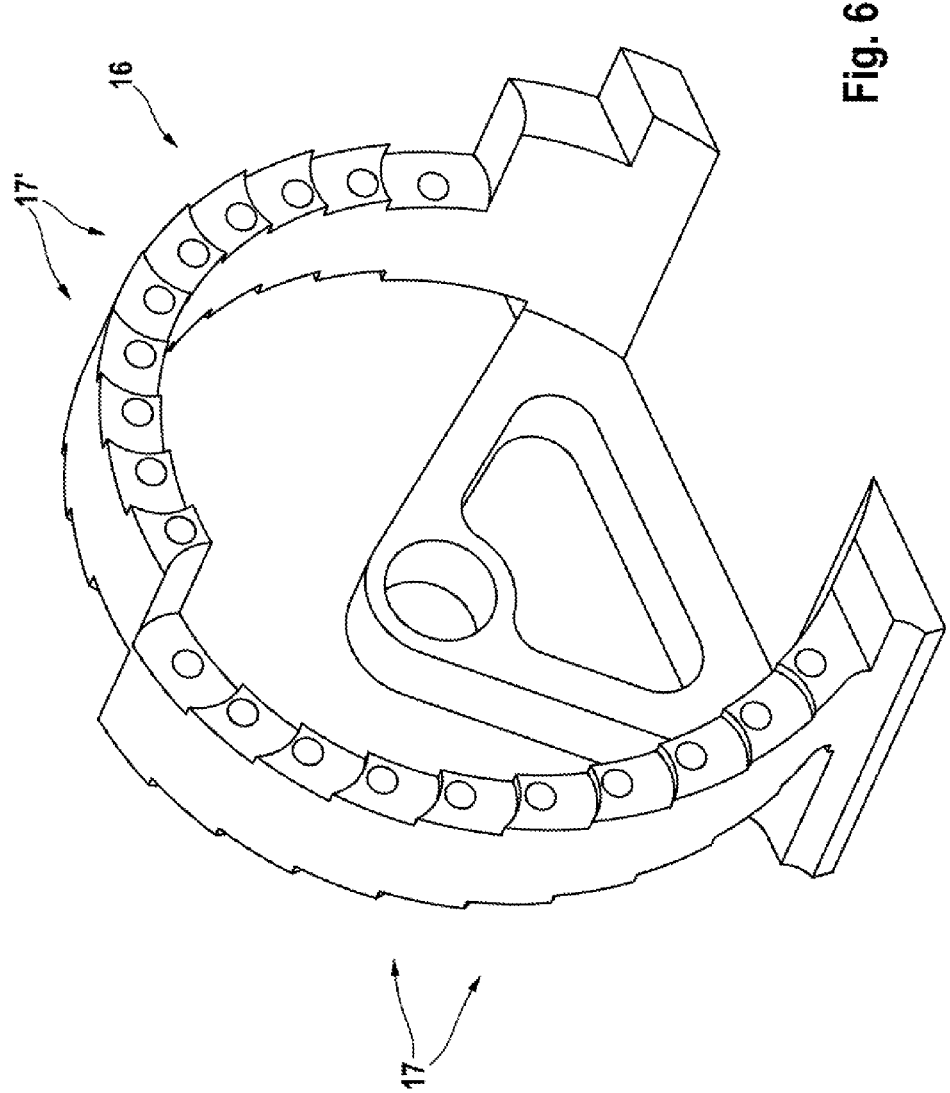

FIG. 6 shows a bearing block 16 for an arrangement of motor bearings 20 with motors 12, 12', 12", . . . and pinions 13, 13', 13" . . . . This bearing block 16 may be constructed in such a way that it can bear motor bearings 20 on both sides, thereby making an arrangement of a multitude of motors 12, 12', 12", . . . possible. In the case of the bearing block 16 shown, for example, 40 motors 12, 12', 12", . . . to drive a set 4 or 4' of leaves 3, 3', 3" . . . are possible. This number may of course be reduced or be further increased. In the case of bearing block 16 it can also be seen that the motor bearings 20 (see FIG. 7) can be arranged in at least two gradations 17 and 17' in order to be able to realize the arrangement principle described in FIG. 4.

Figure 7:
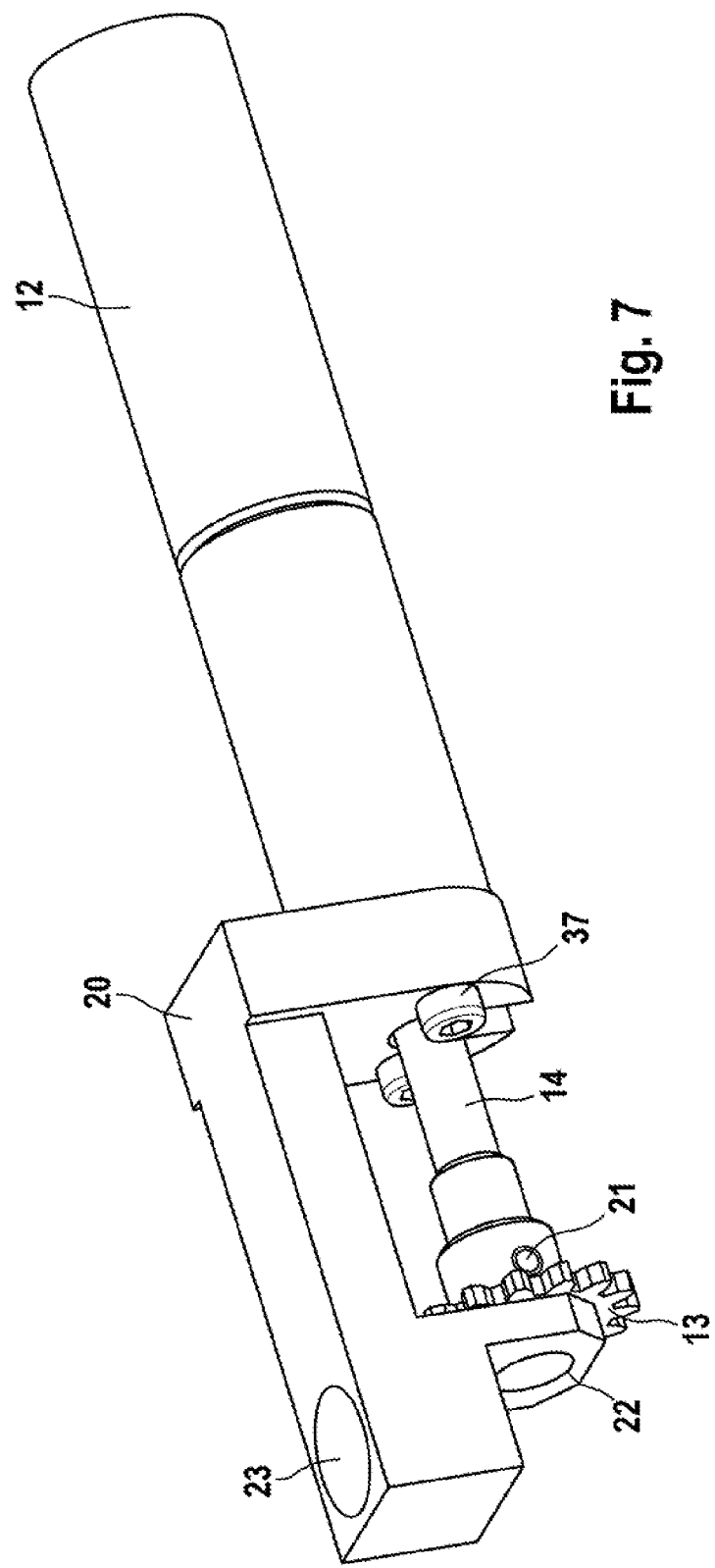

FIG. 7 shows a motor bearing 20 to which a motor 12 has been added by means of motor mountings 37 so that an axle 14 is located in a bearing 22. As an example, the axle 14 may fully or partially be made of steel. A pinion 13 is positioned onto this axle 14 by means of a mounting 21, for example a bolt. A boring 23 may serve the attachment of the motor bearing 20 on the bearing block 16.

All motor bearings 20 of this type may be constructed in the same manner using the bearing blocks 16 described above since the bearing block 16 already may provide the gradations 17, 17' for the positioning of the pinions 13, 13', 13", . . . according to their engagement with the motor-side gear segments 10, 10', 10", . . . .

Figure 8:
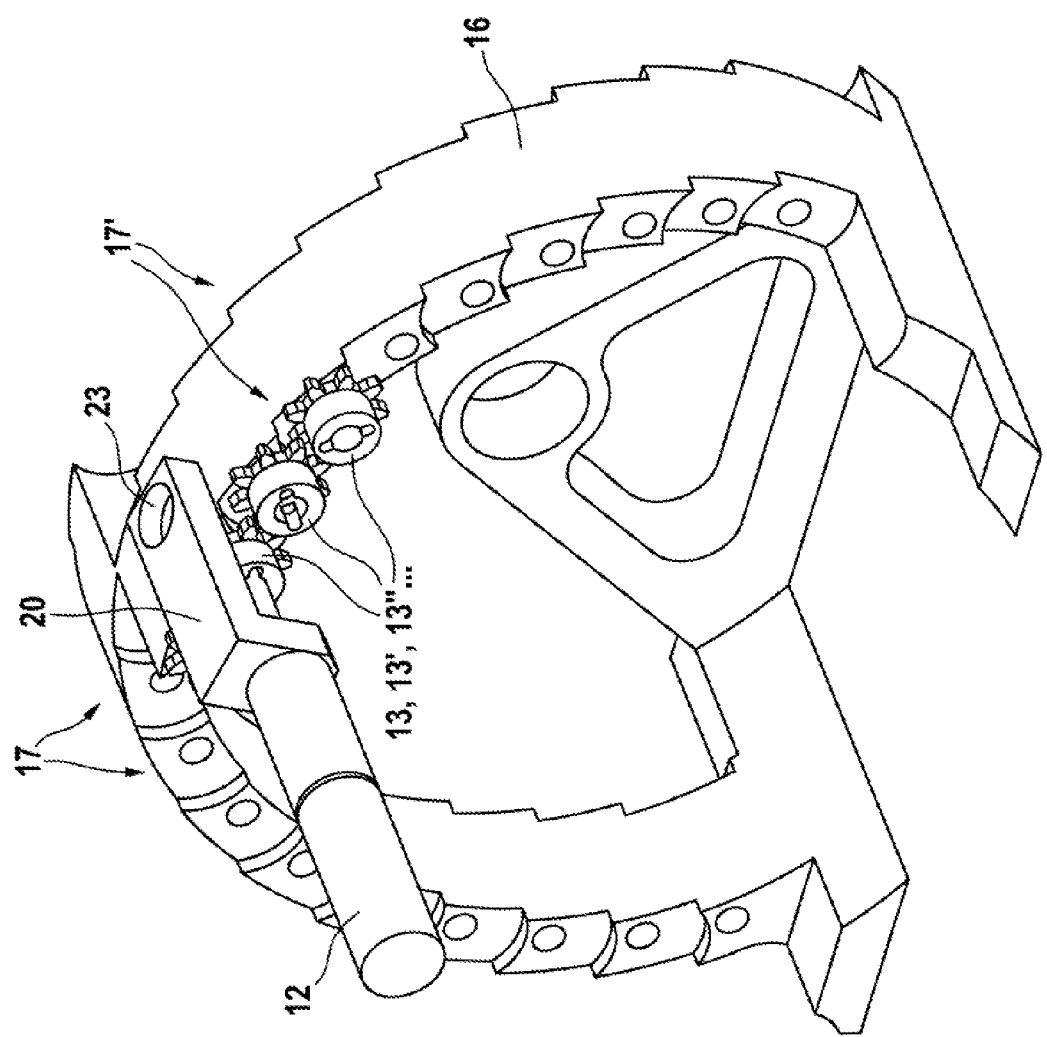

FIG. 8 shows by way of an example of a motor bearing 20 the latter's attachment to a bearing block 16. The pinions 13, 13', 13", . . . drawn in without the motor bearing 20 illustrate how they are positioned in gradated fashion. In this way, such a bearing block 16 presets the respective gradations 17 and 17' for the arch-shaped sequence 31 of motors 12, 12', 12", . . . , preferably on the front side as well as on the rear side of the bearing block 16 so that a great number of motors 12, 12', 12", . . . can be arranged in accordance with the principle described.

Figure 9:
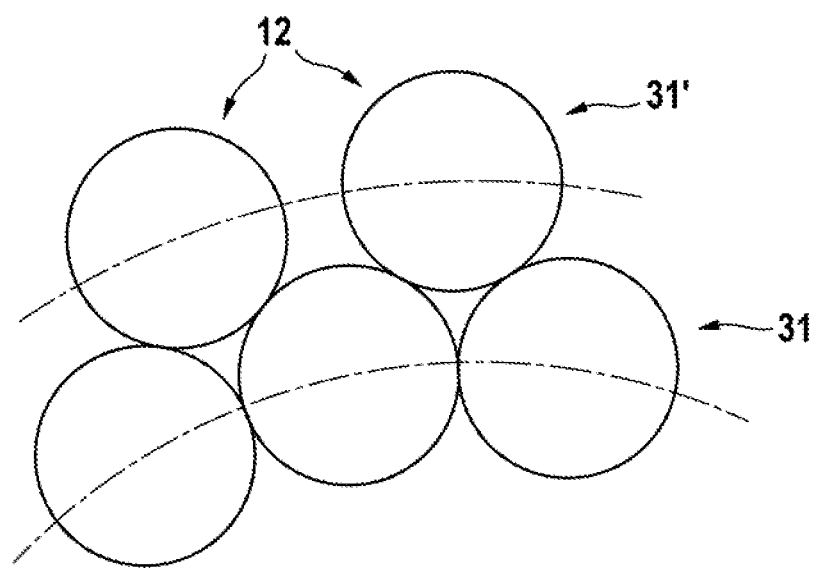

FIG. 9 also shows a schematic diagram of a further embodiment by means of which even more motors 12, 12', 12", . . . can be positioned. If one arranges segment discs 11, 11', 11", . . . of a package 15 in such a way that in a center sector of the package 15 of segment discs 11, 11', 11", . . . , motor-side gear segments 10, 10', 10", . . . are located on a larger radius than further outside in the package 15, motors 12, 12', 12", . . . can be provided in two arch-shaped sequences 31, 31' lying on top of each other. In this way, it will be possible to arrange even more motors 12, 12', 12", . . . in order to drive even more leaves 3, 3', 3", . . . in a manner in accordance with the invention if, for example, thinner leaves 3, 3', 3", . . . are provided for a better recreation of the re-created shape 6' of a treatment object 6, or if the multi-leaf collimator 1 has a relatively large-area design in order to irradiate large treatment objects 6. In any event, in this way leaf drives 2 may also be constructed that are equipped with over 100 leaves 3, 3', 3", . . . per set 4, 4'. Of course, even more tiers of motors 12, 12', 12", . . . will be possible in corresponding fashion as well.

Figure 10A:
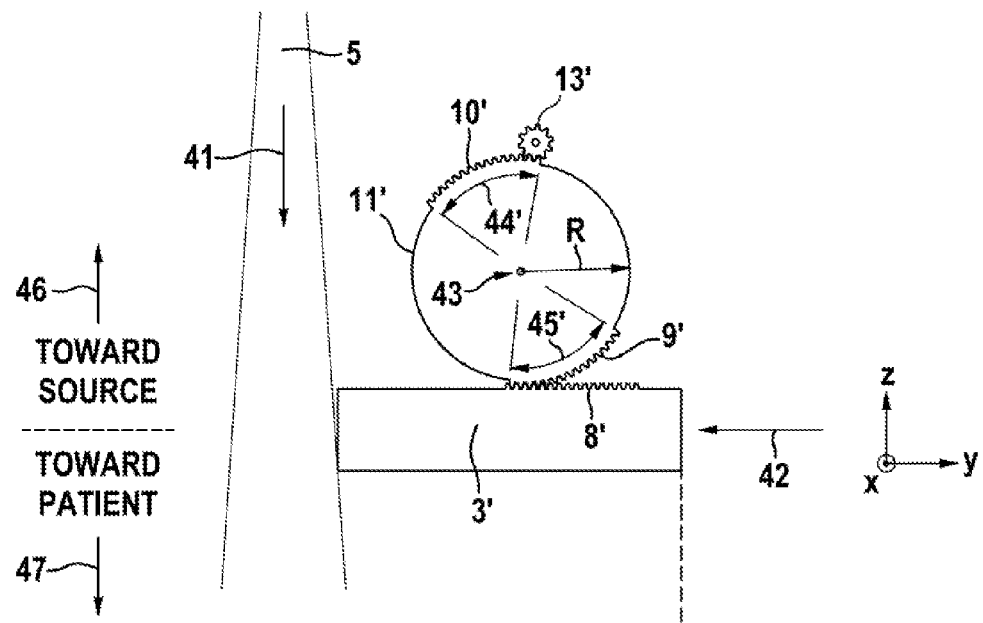
Figure 10B:
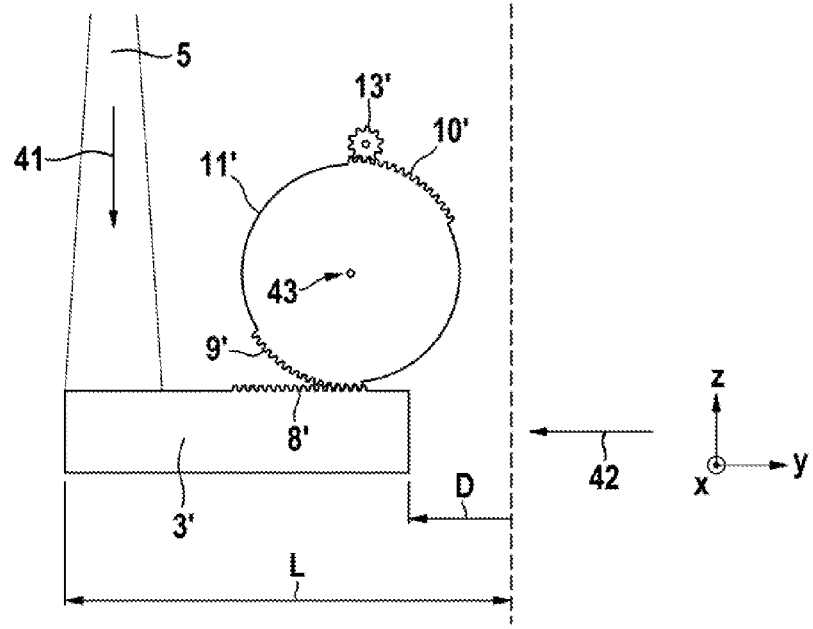

FIGS. 10A-10B illustrate, for purposes of further description of a potential embodiment of the present invention, a conceptual side view of one particular segment disk 11', along with its associated motor-driven pinion 13', and its associated leaf 3' when the leaf 3' is at the two most extreme positions along the direction of displacement 42 of the leaves. FIGS. 11A-11C illustrate, for purposes of further description of a potential embodiment of the present invention, a conceptual side view of two adjacent segment disks 11' and 11", their correspondingly adjacent motor-driven pinions 13' and 13", and their correspondingly adjacent leaves 3' and 3", when the adjacent leaves 3' and 3" are at different combinations of extreme positions along the direction of displacement 42.

Referring now to FIGS. 10A-10B and FIGS. 11A-11C, provided is a multi-leaf collimator 1 (MLC) for controlling a shape of a high-energy beam 5 emanating from a radiation source 25 (not shown) and propagating in a direction of propagation 41. It is to be appreciated that the particular orientation of the elements shown relative to a treatment room coordinate system (e.g. x-y-z axes) in FIGS. 10A-10B is only one special case, because the MLC 1 may be in any of a variety of different orientations during a treatment session. As illustrated in FIGS. 10A-10B, the leaf 3' is individually displaceable relative to all of the other leaves 3, 3", . . . in a direction of displacement 42 that is generally transverse to the direction of propagation 41. The leaves including leaf 3' may have a predefined range of displacement "D" in the direction of displacement 42. The plurality of leaves 3, 3', 3", . . . collectively having a radiation source-facing side 46 (the "upper" side in FIGS. 10A-10B) and a patient-facing side 47 (the "lower" side) opposite the radiation source-facing side 46.

Shown on the leaf 3' is the rack gear 8' extending along the direction of displacement 42. As illustrated, the individually rotatable segment disks 11, 11', 11", . . . including segment disk 11' are preferably disposed on the radiation source-facing side 46 of the plurality of leaves 3, 3', 3", . . . , adding to the space savings and other advantages of the present invention. The plurality of segment disks 11, 11', 11", . . . . Preferably are positioned side by side along a common axis of rotation 43 that is generally transverse to both the direction of propagation 41 and the direction of displacement 42. Each segment disk 11, 11', 11", . . . corresponds to a respective one of the leaves 3, 3', 3", . . . .

Referring now to the segment disk 11' of FIGS. 10A-10B, the segment disk 11' includes a leaf-side gear segment 9' formed along a first peripheral portion 45' thereof that is engaged with the rack gear 8' of the leaf 3'. The leaf 3' is displaced in the direction of displacement 42 according to a motor-controlled rotation of the segment disk 11' around the common axis of rotation 43 as provided by the motor-driven pinion 13'. The motor-driven pinion 13' is engaged with the motor-side gear segment 10' formed along a second peripheral portion thereof 44' of the segment disk 11'.

Preferably, in one particularly advantageous embodiment of the present invention, the segment disk 11' has a radius R that is sufficiently comparable to the predefined range of displacement D of the leaf 3' such that the leaf 3' can be fully displaced through its range of displacement D in less than one full turn of the segment disk 11'. This relatively large sizing of the segment disks provides a relatively large circumference along which to position the driving pinions 13, 13', 13", . . . and their associated motors 12, 12', 12", . . . , preferably electrical motors, thereby allowing for a larger number of motorized pinion assemblies to be used, and therefore a larger number of individually controllable segments disks 11, 11', 11", . . . and their corresponding leaves 3, 3', 3", . . . to be accommodated. In one embodiment, the radius R is greater than one-half of D. In another embodiment, the radius R is greater than D. For the particular example of FIGS. 10A-10B, it is also the case that the first peripheral portion 45' of segment disk 11' containing the leaf-side gear segment 9' is non-overlapping with the second peripheral portion 44' containing the motor-side gear segment 10', although it is to be appreciated that the scope of the preferred embodiments is not so limited.

Further illustrated in FIGS. 10A-10B is an overall lateral range "L" that is defined by the lateral size of the leaves in the direction of displacement along with the extent of the predefined range of displacement D. In one embodiment, the plurality of segment disks 11, 11', 11", . . . and the plurality of motors 12, 12', 12", . . . and pinions 13, 13', 13", . . . are configured and dimensioned to be entirely confined within that overall lateral range L on the radiation source-facing side 46 of the plurality of leaves 3, 3', 3", . . . , thereby conveniently occupying a very compact space while at the same time accommodating a relatively large number of individually displaceable leaves 3, 3', 3", . . . .

According to another advantageous embodiment, the motor-side gear segments of any two adjacent segment disks 11, 11', 11", . . . are staggered in such a way that there will be no angular overlap (which can also be referenced as an "abutment") between those motor-side gear segments 10, 10', 10", . . . throughout the predetermined range of displacement of their corresponding leaves 3, 3', 3", . . . . Thus, as illustrated in the example of FIGS. 11A-11C, the motor-side gear segment 10' of segment disk 11' is strategically disposed along the second peripheral portion 44', and in a coordinated fashion the motor-side gear segment 10" of segment disk 11" is strategically disposed along the second peripheral portion 44", both in further coordination with the positioning of motor-driven pinions 13' and 13", such that even at the two relative displacement extremes of leaves 3' and 3" (see FIG. 11B for one extreme and FIG. 11C for the other extreme), there is no angular overlap (abutment) of the motor-side gear segments 10' and 10". This can in turn allow, in accordance with another preferred embodiment, the motor-driven pinions 13' and 13" to be wider than their associated motor-side gear segments 10' and 10", 10", respectively, in the direction of the common axis of rotation 43.

These are just examples of embodiments of a preferred principle of the invention according to which pivotable gear segments 9, 9', 9", . . . and 10, 10', 10", . . . are interposed between the gear rod-like drive engagements 8, 8', 8", . . . of the leaves 3, 3', 3", . . . and the motors 12, 12', 12", . . . with pinions 13, 13', 13", . . . , thereby facilitating a very compact design of the leaf drives 2. This preferred basic idea of the invention makes it possible to realize the compact construction of the leaf drives 2, with the latter being arranged between the leaves 3, 3', 3", . . . and the radiation source 25 without increasing or significantly increasing the size of the irradiation head 38 or occupying additional structural space.

Figure 12A:
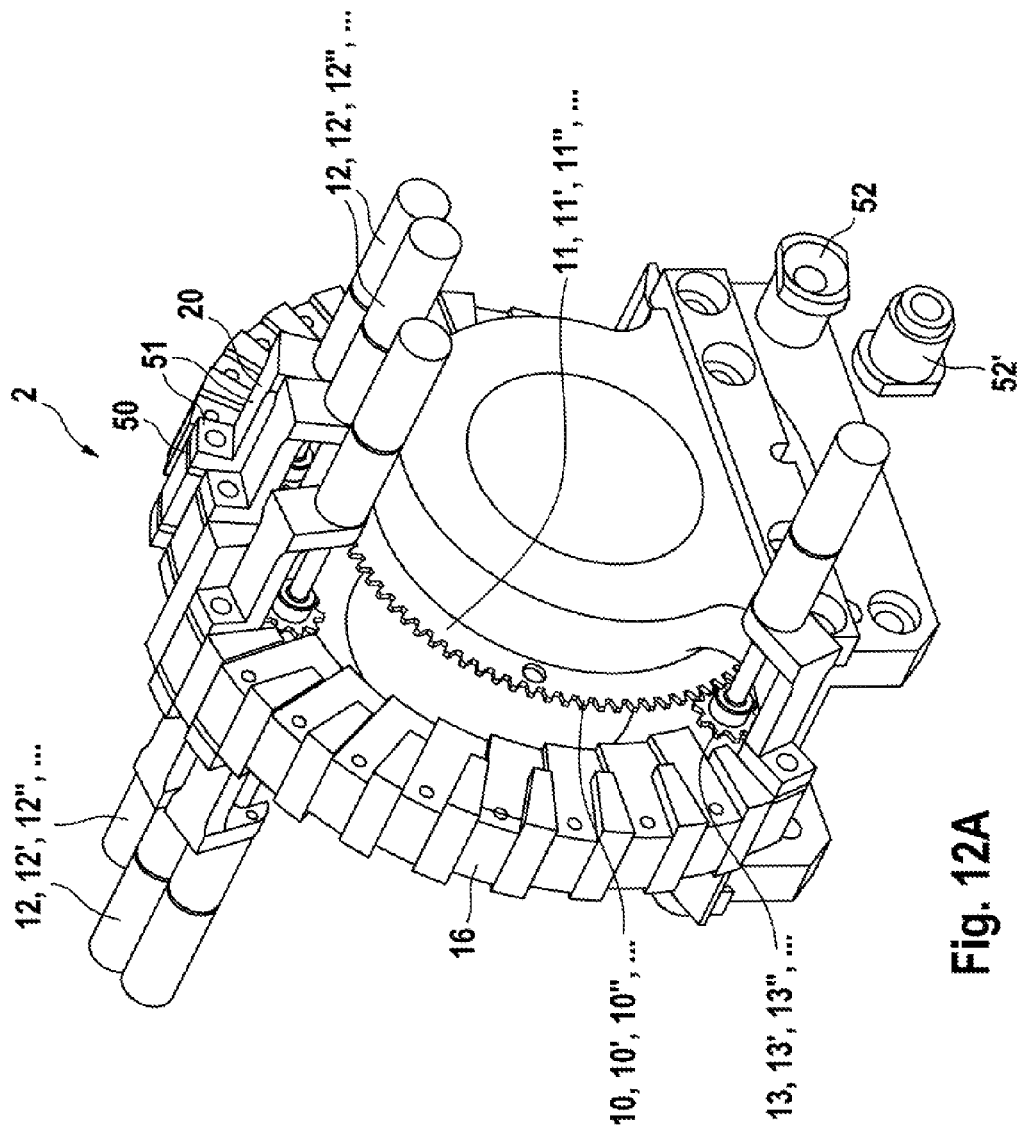

FIGS. 12A to 12C illustrate a further embodiment of the leaf drive 2 for use in a multi-leaf collimator 1. Therein, FIG. 12A shows a partial perspective overview of the leaf drive 2, FIG. 12B shows a more detailed view of a mounting of the motors 12, 12', 12", . . . , and FIG. 12C shows a detailed side view of an adjustable motor mount. For most parts, reference may be made to the embodiments above.

In the embodiment of FIGS. 12A to 12C, several possible options are realized in combination, which also might be realized in an isolated way. Firstly, as shown in detail in FIGS. 12B and 12C, the motors 12, 12', 12", . . . and/or the pinions 13, 13', 13", . . . may be mounted adjustably, such that a relative position of the pinions 13, 13', 13", . . . to the motor-side gear segments 10, 10', 10", . . . may be adjusted. For simplification purposes, in FIGS. 12A-12C, the segmentation of the segment disks 11, 11', 11", . . . is not shown, reference may be made to FIG. 4 in this regard.

In order to allow for an adjustment of this relative position, the motor bearings 20 and/or the bearing block 16 may be designed such that adjustment means or positioning means are provided. As shown in the side view of FIG. 12C, the motor bearings 20 may provide elongated holes 48 or slot holes receiving screws, bolts or any other means (not depicted) for mounting the motor bearings 20 to the bearing block 16. One or more threaded holes 49 and/or other anchoring means may be provided in the bearing block 16 in order to receive the means for mounting the motor bearings 20.

In FIG. 12C, schematically and for illustrative purposes only, three motors 12, 12', 12", . . . are depicted in different adjustment positions with regard to the respective motor-side gear segments 10, 10', 10", . . . . Therein, in the left motor 12, 12', 12", . . . and left pinion 13, 13', 13", . . . , the slack is smallest, whereas in the right motor 12, 12', 12", . . . , and pinion 13, 13', 13", . . . , by increasing the distance between the pinion 13, 13', 13", . . . and the motor-side gear segment 10, 10', 10", . . . , the slack is significantly increased.

Alternatively or additionally, as the skilled person will recognize, other means for positioning the pinions 13, 13', 13", . . . with regard to the motor-side gear segments 10, 10', 10", . . . may be provided. Due to the adjustability, a slackness of the engagement of the pinions 13, 13', 13", . . . with the motor-side gear segments 10, 10', 10", . . . may be adjusted. Consequently, a backlash may be prevented, and production tolerances may be compensated. The negative impacts of these production tolerances, which, typically, may not fully be avoided, thus may be greatly reduced.

Further, FIGS. 12A to 12C, show an additional option regarding the design of the motor bearings 20. As shown in FIG. 12B, the motor bearings 20 each may comprise several components. Thus, each motor bearing 20 may comprise an axle bearing 50 for mounting and bearing the axle 14. As an example, the axle bearing 50 may have the shape of a perforated plate having a bearing or bore (not visible) receiving the axle 14. The axle bearing preferably may be made of a material having a high stability against abrasion, such as bronze and/or brass, specifically bearing bronze. Additionally, the motor bearings 20 each may comprise at least one motor holder 51 for mounting the motors 12, 12', 12", . . . . The axle bearings 50 may be interposed in between the motor holders 51 and the bearing block 16 and may be held in place by clamping forces. In order to save weight, the motor holders may be made of a lighter material, such as aluminum.

As outlined above, the position of the pinions 13, 13', 13", . . . may be adjustable, in order to eliminate slackness and/or in order to compensate production tolerances. Similarly, additionally or alternatively, the leaf drives 2, i.e. all of the leaf drives, some of the leaf drives or all of the leaf drives 2 may be mounted adjustably such that a position of the leaf drives 2 relative to the leaves 3, 3', 3'', . . . may be adjusted. For this purpose, an adjustment mechanism may be provided.

In FIG. 12A, one potential embodiment of an adjustable mounting of the leaf drive 2 is depicted. In this embodiment, one or more excenters 52, 52' are used to adjust a height of the whole block comprising the leaf drive 2 with its components, such as forty segmented disks 11, 11', 11'', . . . , forty motors 12, 12', 12'', . . . and pinions 13, 13', 13'', as well as the bearing block 16, relative to the leaves 3, 3', 3'', . . . . In FIG. 12A, one of the excenters 52 is depicted in an application orientation, whereas, for illustrative purposes, one excenter 52' is depicted in reverse orientation, in order to illustrate the excentric tip of the excenter 52' facing towards the leaf drive 2. The excenters 52, 52' may be supported by a base or leaf drive bearing, which is not depicted in the figures.

By using the excenter 52, 52', the whole leaf drive 2 may easily be lifted or lowered over a base (not depicted) serving as a bearing for the whole leaf drive 2. Since the leaves 3, 3', 3'', . . . typically are guided in appropriate guide elements, the gear rod-like drive engagements 8, 8', 8'', . . . typically all are equal in height. By adjusting the height of the whole leaf drive 2 over these gear rod-like drive engagements 8, 8', 8'', . . . by using the one or more excenters 52, 52', the slack may be reduced. Thereby, the backlash may be reduced, and the positioning precision of the leaves 3, 3', 3'', . . . may be increased.

List Of Reference Symbols
1 multi-leaf collimator
2 leaf drive
3, 3', 3'', . . . leaves
3A leaves separated
3B leaves moved together
4, 4' set of leaves
5 high-energy beam
6 treatment object
6' re-created shape of the treatment object
7 double arrow: displacement direction of the leaf
8, 8', 8'', . . . gear rod-like drive engagement (also called "rack gear")
9, 9', 9'', . . . leaf-side gear segment
10, 10', 10'', . . . motor-side gear segment
11, 11', 11'', . . . segment disk
12, 12', 12'', . . . motor
13, 13', 13'', . . . pinion
14 axle
15 package of segment disks
16 bearing block
17, 17' gradation
20 motor bearings
21 mounting
22 bearing
23 boring
24, 24', 24'', . . . spacer
25 radiation source
26 beams
27 gap
28 center at which imaginary continuations of the leaf delimitations converge
29 front face of the leaves
30 center plane of the multi-leaf collimator
31, 31' arched-shaped sequence of motors
32 holes
33 axle
34 bearing block
35 base frame
36 guiding device
37 motor mounting
38 irradiation head
39 free structural space
41 direction of propagation
42 direction of displacement
43 axis of rotation
44', 44'' second peripheral portion
45' first peripheral portion
46 radiation source-facing side
47 patient-facing side
48
49
50
51
52 elongated hole
threaded hole
axle bearing
motor holder
excenter in application orientation
52' excenter in reverse orientation (for illustrative purposes)

The invention claimed is:

1. Multi-leaf collimator with leaf drives, with two sets of displaceable leaves arranged side by side of each other and facing each other in order to impress a high-energy beam with the shape of an irregularly formed treatment object by enabling each of the leaves to assume a position oriented along the shape of the treatment object by means of the leaf drives, with the leaf drives being designed in such a way that the leaves are each equipped with a gear rod-like drive engagement in a direction of displacement,
   wherein a pivotable leaf-side gear segment located, together with a motor-side gear segment on a segment disk, engages with the gear rod-like drive engagement, with a pinion drivable by a motor engaging with the motor-side gear segment, wherein the segment disks are arranged side by side for each set of leaves as a package on one axle, and wherein the motor-side gear segments of two segment disks located next to each other are staggered in such a way that they will not abut each other.

2. Multi-leaf collimator in accordance with claim 1, characterized in
   that the pinions are wider than the motor-side gear segments.

3. Multi-leaf collimator in accordance with claim 1, characterized in
   that the motors for each package of segment discs in an engagement range of the respective motor-side gear segments are arranged in series in the shape of an arch.

4. Multi-leaf collimator in accordance with claim 3, characterized in
   that the motors are mounted on a bearing block which encompasses in each case a package of segment discs in their circumferential range.

5. Multi-leaf collimator in accordance with claim 4, characterized in
   that the bearing block is equipped on both sides with motors.

6. Multi-leaf collimator in accordance with claim 4, characterized in
   that the bearing block positions the pinions indirectly or directly by means of positioning agents in their engagement position opposite the motor-side gear segments.

7. Multi-leaf collimator in accordance with claim 6, characterized in
that the pinions are mounted on axles supported by motor bearings and the latter are mounted on the bearing block.

8. Multi-leaf collimator in accordance with claim 7, characterized in
that the motor bearings each comprise a motor holder for mounting the motor and an axle bearing for bearing the axle.

9. Multi-leaf collimator in accordance with claim 8, characterized in
that the motor holders are made of aluminum and/or titanium and the axle bearings are made of bronze and/or brass.

10. Multi-leaf collimator in accordance with claim 3, characterized in
that a step-like gradation of an arrangement of the pinions driven by the motors is provided for their engagement with the various motor-side gear segments.

11. Multi-leaf collimator in accordance with claim 10, characterized in
that at least two step-like gradations are provided, with segment discs located next to each other being driven by motors with pinions assigned to various ones of these step-like gradations and the motor-side gear segments of segment discs lying next to each other being located in different areas of the circumference of the package of segment discs.

12. Multi-leaf collimator in accordance with claim 3, characterized in
that due to an arrangement of motor-side gear segments on corresponding varying radii of the segment discs, the motors are arranged in arch-shaped sequences lying on top of each other.

13. Multi-leaf collimator in accordance with claim 1, characterized in
that, relative to its width, the gear rod-like drive engagement of the leaves is designed differently from the width of the leaf-side gear segment.

14. Multi-leaf collimator in accordance with claim 1, characterized in
that the leaf drives are mounted adjustably such that a position of the leaf drives relative to the leaves may be adjusted.

15. Multi-leaf collimator in accordance with claim 14, characterized in
that the position of the leaf drives is adjustable by at least one excenter.

16. Multi-leaf collimator in accordance with claim 1, characterized in
that spacers are provided between adjoining segment discs that reduce mutual friction to the largest extent.

17. Multi-leaf collimator in accordance with claim 1, characterized in
that the leaves have a trapezoid cross section to the effect that they taper in the direction of a radiation source corresponding approximately to a divergence of the high-energy beam.

18. Multi-leaf collimator in accordance with claim 17, characterized in
that the sets of leaves are tilted relative to an optical path to the effect that no rays can pass through a gap between the leaves.

19. Multi-leaf collimator in accordance with claim 1, characterized in
that the leaf drives are designed in such a way that the leaves of the two sets of leaves can come in contact with each other with their front faces only outside of a center plane of the multi-leaf collimator.

20. Multi-leaf collimator in accordance with claim 1, characterized in
that the pinions and/or the motors are mounted adjustably such that a relative position of the pinions with regard to the motor-side gear segments may be adjusted.

21. A multi-leaf collimator (MLC) for controlling a shape of a high-energy radiation beam emanating from a radiation source and propagating in a direction of propagation, comprising:
a plurality of leaves individually displaceable in a direction of displacement that is generally transverse to the direction of propagation, said plurality of leaves having a predefined range of displacement in said direction of displacement, each said leaf including a rack gear extending along the direction of displacement;
a plurality of individually rotatable segment disks positioned side by side along a common axis of rotation that is generally transverse to said direction of propagation and to said direction of displacement, each said segment disk corresponding to a respective one of said leaves, each said segment disk including a leaf-side gear segment formed along a first peripheral portion thereof that is engaged with said rack gear of the corresponding leaf to displace that leaf along said direction of displacement according to a motor-controlled rotation of said segment disk around said common axis of rotation; and
a plurality of motor-driven pinions, each said motor-driven pinion being engaged with a respective one of said segment disks along a motor-side gear segment formed along a second peripheral portion thereof to provide said motor-controlled rotation thereof;
wherein the motor-side gear segments of any two adjacent segment disks are staggered in such a way that they will not abut each other throughout the range of displacement of their corresponding leaves.

22. The MLC of claim 21, each said motor-driven pinion being coupled to a distinct electrical motor to form a respective plurality of motor-pinion assemblies, wherein said plurality of motor-pinion assemblies are arranged in an arch-like pattern relative to said common axis of rotation of said plurality of segment disks.

23. The MLC of claim 22, wherein said motor-pinion assemblies are mounted on a common bearing block extending peripherally around said plurality of segment disks in an arch-like shape relative to said common axis of rotation, said motor-pinion assemblies being mounted on respective step-like gradations formed in said bearing block along the direction of said common axis of rotation for achieving respective engagement of said motor-driven pinions with said motor-side gear segments of said segment disks.

24. The MLC of claim 21, wherein said motor-driven pinions are wider than their associated motor-side gear segments in a direction of said common axis of rotation.

25. The MLC of claim 24, further comprising a spacer agent disposed between each adjacent pair of said segment disks for reducing mutual friction therebetween.

26. The MLC of claim 21, said plurality of leaves, said plurality of segment disks, and said plurality of motor-driven pinions collectively forming a first leaf/drive assembly, wherein the MLC further comprises a second leaf/drive assembly generally similar to said first leaf-drive assembly and disposed on an opposing side of a center plane of the MLC.

27. The MLC of claim 21, said plurality of leaves collectively having a radiation source-facing side and a patient-facing side opposite said radiation source-facing side, wherein said plurality of segment disks are disposed on said radiation source-facing side of said plurality of leaves, and wherein each of said plurality of segment disks has a radius along said first and second peripheral portions thereof that is sufficiently comparable to said predefined range of displacement of said leaves such that each said leaf can be fully displaced through its range of displacement in less than one full turn of said segment disk, whereby structural compactness of the MLC is facilitated.

28. The MLC of claim 27, said plurality of leaves in conjunction with said predefined range of displacement defining an overall lateral range (L) in said direction of displacement, wherein said plurality of segment disks and said plurality of motor-pinion assemblies are configured and dimensioned to be entirely confined within said overall lateral range on said radiation source-facing side of said plurality of leaves.

29. The MLC of claim 28, wherein said segment disk radius is greater than one-half of said predefined range of displacement of said leaves.

30. The MLC of claim 29, wherein said segment disk radius is greater than said predefined range of displacement of said leaves.

31. The MLC of claim 21, wherein, for each of said segment disks, said first peripheral portion thereof containing said leaf-side gear segment is non-overlapping with said second peripheral portion thereof containing said motor-side gear segment.

32. A multi-leaf collimator (MLC) for controlling a shape of a high-energy radiation beam emanating from a radiation source and propagating in a direction of propagation, comprising:
a plurality of leaves individually displaceable in a direction of displacement that is generally transverse to the direction of propagation, said plurality of leaves having a predefined range of displacement in said direction of displacement, said plurality of leaves collectively having a radiation source-facing side and a patient-facing side opposite said radiation source-facing side, each said leaf including a rack gear extending along the direction of displacement;
a plurality of individually rotatable segment disks disposed on said radiation source-facing side of said plurality of leaves, said plurality of segment disks being positioned side by side along a common axis of rotation that is generally transverse to said direction of propagation and to said direction of displacement, each said segment disk corresponding to a respective one of said leaves, each said segment disk including a leaf-side gear segment formed along a first peripheral portion thereof that is engaged with said rack gear of the corresponding leaf to displace the corresponding leaf according to a motor-controlled rotation of said segment disk around said common axis of rotation; and
a plurality of motor-driven pinions, each said motor-driven pinion being engaged with a respective one of said segment disks along a motor-side gear segment formed along a second peripheral portion thereof to provide said motor-controlled rotation thereof;
wherein each of said plurality of segment disks has a radius along said first and second peripheral portions thereof that is sufficiently comparable to said predefined range of displacement of said leaves such that each said leaf can be fully displaced through its range of displacement in less than one full turn of said segment disk;
whereby structural compactness of the MLC is facilitated.

33. The MLC of claim 32, each said motor-driven pinion being coupled to a distinct electrical motor to form a respective plurality of motor-pinion assemblies, wherein said plurality of motor-pinion assemblies are arranged in an arch-like pattern relative to said common axis of rotation of said plurality of segment disks.

34. The MLC of claim 33, wherein said motor-pinion assemblies are mounted on a common bearing block extending peripherally around said plurality of segment disks in an arch-like shape relative to said common axis of rotation, said motor-pinion assemblies being mounted on respective step-like gradations formed in said bearing block along the direction of said common axis of rotation for achieving respective engagement of said motor-driven pinions with said motor-side gear segments of said segment disks.

35. The MLC of claim 33, said plurality of leaves in conjunction with said predefined range of displacement defining an overall lateral range in said direction of displacement, wherein said plurality of segment disks and said plurality of motor-pinion assemblies are configured and dimensioned to be entirely confined within said overall lateral range on said radiation source-facing side of said plurality of leaves.

36. The MLC of claim 32, wherein said segment disk radius is greater than one-half of said predefined range of displacement of said leaves.

37. The MLC of claim 36, wherein said segment disk radius is greater than said predefined range of displacement of said leaves.

38. The MLC of claim 32, wherein the motor-side gear segments of any two adjacent segment disks are staggered in such a way that there will be no angular overlap therebetween throughout the range of displacement of their corresponding leaves.

39. The MLC of claim 38, wherein said motor-driven pinions are wider than their associated motor-side gear segments in a direction of said common axis of rotation.

40. The MLC of claim 39, further comprising a spacer agent disposed between each adjacent pair of said segment disks for reducing mutual friction therebetween.

41. The MLC of claim 32, said plurality of leaves, said plurality of segment disks, and said plurality of motor-driven pinions collectively forming a first leaf/drive assembly, wherein the MLC further comprises a second leaf/drive assembly generally similar to said first leaf-drive assembly and disposed on an opposing side of a center plane of the MLC.

42. The MLC of claim 32, wherein, for each of said segment disks, said first peripheral portion thereof containing said leaf-side gear segment is non-overlapping with said second peripheral portion thereof containing said motor-side gear segment.

* * * * *